United States Patent
Possemiers et al.

(10) Patent No.: US 11,324,717 B2
(45) Date of Patent: May 10, 2022

(54) MICROBIAL CAROTENOIDS AFFECTING GUT MICROBIAL COMPOSITION

(71) Applicant: Microbial Research Management Health NV, Ghent (BE)

(72) Inventors: Sam Possemiers, Merelbeke (BE); Cindy Duysburgh, Wingene (BE); Iris Pinheiro, Merelbeke (BE); Selin Bolca, Gentbrugge (BE); Pieter Van Den Abbeele, Lokeren (BE); Massimo Marzorati, Brussels (BE)

(73) Assignee: Microbial Research Management Health NV, Ghent (BE)

( * ) Notice: Subject to any disclaimer, the term of this patent is extended or adjusted under 35 U.S.C. 154(b) by 15 days.

(21) Appl. No.: 16/311,431

(22) PCT Filed: Jun. 22, 2017

(86) PCT No.: PCT/EP2017/065348
§ 371 (c)(1),
(2) Date: Dec. 19, 2018

(87) PCT Pub. No.: WO2017/220708
PCT Pub. Date: Dec. 28, 2017

(65) Prior Publication Data
US 2019/0209516 A1 Jul. 11, 2019

(30) Foreign Application Priority Data
Jun. 22, 2016 (EP) .................................. 16175832

(51) Int. Cl.
| | | |
|---|---|---|
| A61K 31/35 | (2006.01) | |
| A61K 31/351 | (2006.01) | |
| A61K 35/741 | (2015.01) | |
| A61K 31/7028 | (2006.01) | |
| A61P 1/00 | (2006.01) | |
| A61K 35/00 | (2006.01) | |
| A61K 35/742 | (2015.01) | |
| A61K 35/74 | (2015.01) | |

(52) U.S. Cl.
CPC ........ *A61K 31/351* (2013.01); *A61K 31/7028* (2013.01); *A61K 35/741* (2013.01); *A61P 1/00* (2018.01); *A61K 35/74* (2013.01); *A61K 35/742* (2013.01); *A61K 2035/115* (2013.01)

(58) Field of Classification Search
CPC ........ A61K 31/351; A61K 35/741; A61P 1/00
See application file for complete search history.

(56) References Cited

FOREIGN PATENT DOCUMENTS

| WO | 2007066108 A1 | 6/2007 |
|---|---|---|
| WO | 2012017199 A1 | 2/2012 |

OTHER PUBLICATIONS

Cecil Textbook of Medicine, 20th Edition, vol. 1, 1996.*
Gura et al. (Science 1997).*
Johnson et al., (British J. of Cancer 2001).*
Chen et. al., Journal of Medicinal Chemistry, 2001, American Chemical Society, vol. 44, pp. 2374-2377.*
Extended European Search Report dated Nov. 29, 2016 in reference to co-pending European Patent Application No. 16175832.1.
Charlotte Sy et al, "Interactions between Carotenoids from Marine Bacteria and Other Micronutrients: Impact on Stability and Antioxidant Activity", Marine Drugs, vol. 13, No. 12, Nov. 19, 2015, pp. 7020-7039.
Laura Perez-Fons et al, "Identification and the developmental formation of carotenoid pigments in the yellow-orangespore-formers", Biochimica et Biophysica Acta (BBA)—Molecular and Cell Biology of Lipids, Elsevier, Amsterdam, NL, vol. 1811, No. 3, Dec. 17, 2010, pp. 177-185.
H.A. Hong et al, "The safety of Bacillus subtilis and Bacillus indicus as food probiotics", Journal of Applied Microbiology, vol. 105, No. 2, Aug. 1, 2008, pp. 510-520.
Kazutoshi Shindo et al, "Methyl Glucosyl-3,4-dehydro-appo-8'-lycopenoate, a Novel Antioxidative Glyco-C30-carotenoic Acid Produced by a Marine Bacterium Pianococcus maritimus", The Journal of Antibiotics, vol. 61, No. 12, Dec. 1, 2008, pp. 729-735.
Anonymous: "Final Report Summary—Carodel (Use of Microorganisms for Carotenoids Delivery: Next Generation of Probiotics for Cardiovascular Disease)", European Commission: Cordis: Projects & Results Service, Jun. 3, 2016, pp. 1-3.
Kaulmann Anouk et al: "Carotenoids, inflammation, and oxidative stress-implications of cellular signaling parthways and relation to chronic disease preven", Nutrition Research, Elsevier Inc, vol. 34, No. 11, Jul. 18, 2014, pp. 907-929.
International Search Report and Written Opinion dated Sep. 25, 2017 in reference to International Application No. PCT/EP2017/065348.
Flint et al.; "Diversity, metabolism and microbial ecology of butyrate-producing bacteria from the human large intestine"; Federation of European Microbiological Societies; Feb. 13, 2009; pp. 1-8.
H.M. Hammer, et al.; "Review article: the role of butyrate on colonic function"; Alementary Pharmacology & Therapeutics; 2008; pp. 104-119.

(Continued)

*Primary Examiner* — Shobha Kantamneni
(74) *Attorney, Agent, or Firm* — Dinsmore & Shohl LLP

(57) ABSTRACT

The present invention relates to the use of carotenoids, in particular a microbial carotenoid compound of formula I, such as methyl-glycosyl-apo-8'-lycopenoate or glycosyl-apo-8'-lycopene, for restoring and/or maintaining a health-beneficial gut microbial composition in a subject. The invention further provides the use of said compound in the treatment of disorders associated with a disturbed intestinal barrier integrity, such as for example irritable bowel syndrome. Further, a compound or composition comprising a microbial carotenoid compound is disclosed for use in the prevention and/or treatment of disorders associated with disturbed intestinal barrier integrity.

9 Claims, 13 Drawing Sheets

(56) References Cited

OTHER PUBLICATIONS

Le Gall, et al.; "Comparative effect of orally administered sodium butyrate before or after weaning on growth and several indices of gastrointestinal biology of piglets"; British Journal of Nutrition; 2009; pp. 1285-1296.

Martinez, et al.; "Diarrhoea-predominant irritable bowel syndrome: an organic disorder with structural abnormalities in the jejunal epithelial barrier"; Gut; 2013; 62; pp. 1160-1168.

McCullough, et al.; "The effect of vitamin A on epithelial integrity"; Proceedings of the Nutrition Society; 1999; pp. 289-293.

Piche, et al.; "Impaired intestinal barrier integrity in the colon of patients with irritable bowel syndrome: involvement of soluble mediators"; Gut 2009; 58; pp. 196-201.

Pozuelo, et al.; "Reduction of butyrate- and methane-producing mciroorganisms in patients with Irritable Bowel Syndrom"; Nature—Scientific Reports; 2015; pp. 1-12.

Palozza, et al.; "β-Carotene at High Concentrations Induces Apoptosis by Enhancing Oxy-Radical Production in Human Adenocarcinoma Cells"; Free Radical Biology & Medicine; vol. 30, No. 9; 2001; pp. 1000-10007.

Possemiers, et al.; A Dried Yeast Fermentate Selectively Modulates both the Luminal and Mucosal Gut Mirobiota and Protects against Inflammation, As Studied in an Integrated in Vitro Approach; Journal of Agricultural and Food Chemistry; 2013; pp. 9380-9392.

Venkatraman, et al.; "Increased Permeability in Dextran Sulphate Colitis in Rats: Time Course of Development and Effect of Butyrate"; Scandinavian Journal of Gastroenterology; 2013; pp. 1053-1059.

Vieira, et al.; "Carotenoids, Retinol, and Intestinal Barrier Function in Children from Northeastern Brazil"; Journal of Pediatric Gastroenterology and Nutrition; 2008; pp. 652-659.

Wijtten; et al.; "Intestinal barrier function and absorption in pigs after weaning; a review"; British Journal of Nutrition; 2011; 105; pp. 967-981.

Zhang, et al.; "Cartinoids Up-Regulate Connexin43 Gene Expression Independent of Their Provitamin A or Antioxidant Properties"; Cancer Research; Oct. 15, 1992; 52; pp. 5707-5712.

\* cited by examiner

A

B

A

B

A

B

A

B

A

B

MICROBIAL CAROTENOIDS AFFECTING GUT MICROBIAL COMPOSITION

FIELD OF THE INVENTION

The present invention relates to carotenoids, in particular a microbial carotenoid compound of formula I, such as methyl-glycosyl-apo-8'-lycopenoate or glycosyl-apo-8'-lycopene, for use in restoring and/or maintaining a health-beneficial gut microbial composition in a subject. The invention further provides said compound for use in the treatment and/or prevention of disorders associated with a disturbed intestinal barrier integrity, such as for example irritable bowel syndrome.

BACKGROUND TO THE INVENTION

Carotenoids have recently gained a lot of interest in the functional food industry due to their potential health benefits. Originally found in plants, serving as an accessory pigment during photosynthesis, carotenoids are lipophilic anti-oxidants that have been linked to a decreased risk of cardiovascular disease, macular degeneration and other chronic diseases. While carotenoid production has also been found in some bacteria and fungi for protection against UV damage and oxidative stress, humans and other animals are unable to synthesize carotenoids, and therefore they should be supplied through the diet. The absorption of carotenoids from the diet depends upon efficient release of the carotenoids from the food matrix and subsequent solubilisation by bile acids and digestive enzymes, culminating in their incorporation into mixed micelles. The main part of carotenoid metabolism occurs in the small intestine where they must also be dissolved in dietary lipids before they can passively migrate from the micellar phase in the lumen of the intestine to the lymphatic and blood circulatory system. It is however unknown whether all the carotenoids present in a mixed micelle are absorbed, or whether some are left behind in association with unabsorbed bile salts and cholesterol to be absorbed more distally or lost to the large intestine where they can exert other biological functions.

More than 600 naturally occurring carotenoids have been identified, of which approximately 50 can be converted into retinol (i.e. Vitamin A), and are referred to as provitamin A carotenoids. Provitamin A carotenoids can be converted enzymatically in the intestinal mucosa to yield retinol. Retinol is required for vision, maintenance of differentiated epithelia, mucus secretion and reproduction (McCullough et al., 1999, Proc. Nutr Soc, 58(2)). In humans, provitamin A activity is the only function of carotenoids that is firmly recognized and linked to health outputs. In addition to their provitamin A activity, many carotenoids have been considered to have other biological functions such as the inhibition of lipid peroxidation, tumor suppression, immunomodulation, etc. which are mostly related to their anti-oxidant properties. Cancer-preventive activities of carotenoids have been associated with their anti-oxidant properties and the induction and stimulation of intercellular communication via gap junctions which apply a role in the regulation of cell growth, differentiation and apoptosis. Gap junctional communication between cells appears to be independent of their anti-oxidant property or provitamin A activity (Zhang et al.,1992, Cancer Res 52). Additionally, Vieira et al. (2008, J Pediatr Gastroenterol Nutr 47) have shown that serum concentrations of carotenoids are correlated with gut barrier integrity.

The intestinal epithelial layer is the final barrier between the luminal content and the host. Maintenance of the intestinal barrier function is therefore extremely important for general health and development in humans and animals and consequently intestinal barrier dysfunction plays a pathogenic role in many chronic inflammation-related diseases, such as inflammatory bowel disease (IBD), irritable bowel syndrome (IBS) or metabolic control. Similarly, (lack of) appropriate maturation of gut barrier function has a major impact on animal well-being and productivity in commercial animal production, especially at the sensitive stages in early life conditions (Wijtten et al. 2011, Br J Nutr 105).

The integrity of the intestinal barrier is determined by several factors, including the intestinal mucus layer, epithelial cell proliferation, tight junctions that form the connections between adjacent cells and the microbial composition in the gut. Changes in one of these factors may result in changes in the integrity of the intestinal barrier. For example, in diarrhoea-predominant IBS (IBS-D), electron microscopy studies showed cytoskeleton condensation and enlarged intercellular spaces between epithelial cells, providing the morphological basis for increased intestinal permeability. These structural changes were found to correlate both with mast cell activation and symptoms including diarrhoea and pain (Martinez et al. 2013, Gut 62). These data confirm earlier observations derived from Ussing chamber experiments showing increased permeability in colon tissues of IBS patients (Piche et al., 2009, Gut 58).

The gut microbiota form a complex microbial ecosystem in the gastro-intestinal tract and maintain several essential functions, including colonic fermentation of dietary fibers, extraction of nutrients, synthesis of certain vitamins, prevention against colonization by pathogens, maturation of the intestinal epithelium and immune system, release of metabolites to the systemic tissues, and modulation of gastrointestinal hormone release and nerve function. The gut microbiome consists of the entire microbial community in the human gut including bacteria, yeast, fungi, Archaea, and viruses, resulting in $10^{13}$ to $10^{14}$ microorganisms. Despite the complexity of the ecosystem in the gut, it is mainly represented by a limited number of bacterial phyla, as Firmicutes, Bacteroidetes, Proteobacteria, Fusobacteria, Verrucomicrobia, and Actinobacteria, with Firmicutes and Bacteriodetes as dominant phyla. Within the Firmicutes phylum some important genera are *Faecalibacterium, Bacillus, Clostridium, Lactobacillus* and *Roseburia*. These genera include species that are able to produce butyrate, as they belong to specific *Clostridium* clusters.

Butyrate-producing gut bacteria have recently gained a lot of attention because butyrate plays a key role in maintaining human gut health as the major source of energy to the colonocytes, and as an important regulator of gene expression, inflammation, differentiation and apoptosis in host cells (Hamer et al., 2008, Alimentary Pharmacol. & Therapeutics). A common feature of bowel diseases which are associated with a disrupted gut barrier integrity is a decline in butyrate-producing taxa within the gut microbiome. Pozuela et al. (Nature, 2015) have shown that IBS-D patients are characterized by a reduction of butyrate-producing bacteria, compared to healthy individuals. In particular, butyrate plays important roles at the intestinal level by strengthening the epithelial defence barrier through its effect on mucus production and tight junction expression, resulting in a reduced passage of toxic and pro-inflammatory substances across the intestinal layer. Experiments in a rat model of dextran sulfate sodium (DSS)-induced colitis showed that treatment with butyrate leads to a recovery in transepithelial resistance, which was associated with maintenance of tight junction integrity and inhibition of TNFalpha release (Venkatraman et al., 2000, Scand J Gastroenterol 35). Similarly, butyrate administration to young animals, such as weaned piglets, was shown to stimulate body growth and feed intake, which was associated with improved maturation of the gastrointestinal tract (Le Gall et al. 2009, Br J Nutr 102).

Modulation of the metabolite profile through modulation of the gut microbiota or administration of specific compounds known to modulate the gut microbiota might therefore be used as a potential mode-of-action against disorders associated with impaired intestinal integrity.

The present invention describes a surprisingly improved effect of microbial carotenoids over carotenoids in general on the intestinal barrier integrity by modulating the gut microbial composition towards a more efficient butyrate-producing gut microbial community.

SUMMARY OF THE INVENTION

The inventors have surprisingly found that microbial carotenoid compounds are able to restore and/or maintain a health-beneficial gut microbial composition in subjects. In particular, these microbial carotenoid compounds modulate the gut microbial composition in subjects towards a more efficient butyrate-producing microbial community, thereby affecting the intestinal barrier integrity.

Therefore, in a first aspect, the present invention provides the microbial carotenoid compound of formula (I)

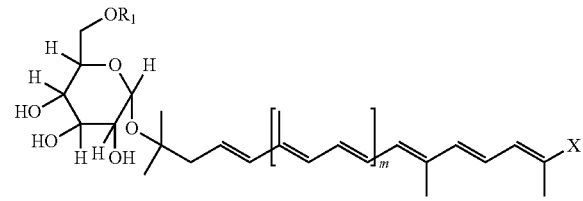

wherein X is $CH_3$ or $COOR_2$ wherein $R_2$ is independently selected from methyl, ethyl, methylethyl, propyl, isopropyl, butyl, isobutyl, sec-butyl and tert-butyl, and wherein m is selected from 0, 1, 2 or 3, and wherein $R_1$ is H or $COC_nH_{2n+1}$ with n being selected from 5, 6, 7, 8, 9, 10, 11, 12, 13 or 14, for use in restoring and/or maintaining a health-beneficial gut microbial composition in a subject.

The present invention further provides said microbial carotenoid compound of formula (I) and as defined above for use in the prevention and/or treatment of increased plasma concentrations of pro-inflammatory cytokines in a subject; in particular in humans.

Further, said microbial carotenoid compound is provided for use in the improvement of exercise performance in humans. In yet another embodiment, the present invention provides said microbial carotenoid compound of formula (I) and wherein X is $CH_3$ or $COOR_2$ wherein $R_2$ is independently selected from methyl, ethyl, methylethyl, propyl, isopropyl, butyl, isobutyl, sec-butyl and tert-butyl, and wherein m is selected from 0, 1, 2 or 3, and wherein $R_1$ is H or $COC_nH_{2n+1}$ with n being selected from 5, 6, 7, 8, 9, 10, 11, 12, 13 or 14, for use in the improvement of gut maturation and gut barrier function in farm animals or fish, or for use in the improvement of production parameters in farm animals or fish.

In still another embodiment, the present invention provides a microbial carotenoid compound of formula (I) and wherein X is $CH_3$ or $COOR_2$ wherein $R_2$ is independently selected from methyl, ethyl, methylethyl, propyl, isopropyl, butyl, isobutyl, sec-butyl and tert-butyl, and wherein m is selected from 0, 1, 2 or 3, and wherein $R_1$ is H or $COC_nH_{2n+1}$ with n being selected from 5, 6, 7, 8, 9, 10, 11, 12, 13 or 14, for use in the prevention and/or treatment of disorders associated with a disturbed intestinal barrier integrity. In a further embodiment, said disorders associated with a disturbed intestinal barrier integrity are selected from the group comprising irritable bowel syndrome, inflammatory bowel disease, intestinal discomfort, diarrhoea, constipation, Crohn's disease, ulcerative colitis, coeliac disease, pouchitis, mucositis, gut infection, gut microbiota dysbiosis, metabolic syndrome, obesity, diabetes, chronic fatigue syndrome, cardiovascular disease, a mental disorder, a neurodegenerative disease, rheumatoid arthritis, spondyloarthritis, a form of cancer or any combination thereof.

The present invention is also directed to a composition comprising a microbial carotenoid compound of formula (I) wherein X is $CH_3$ or $COOR_2$ wherein $R_2$ is independently selected from methyl, ethyl, methylethyl, propyl, isopropyl, butyl, isobutyl, sec-butyl and tert-butyl, and wherein m is selected from 0, 1, 2 or 3, and wherein $R_1$ is H or $COC_nH_{2n+1}$ with n is selected from 5, 6, 7, 8, 9, 10, 11, 12, 13 or 14, for use in the prevention and/or treatment of increased plasma concentrations of pro-inflammatory cytokines in a subject; in particular in humans.

The present invention further relates to a carotenoid compound of formula (I) or a composition comprising a microbial carotenoid compound of formula (I) for use as herein described in the different embodiments above, wherein X is $CH_3$ or $COOCH_3$, wherein m is 3, and wherein $R_1$ is H or $COC_nH_{2n+1}$ with n=5, 6, 7, 8, 9, 10, 11, 12, or 13.

In a preferred embodiment, the present invention relates to a carotenoid compound of formula (I) or a composition comprising a microbial carotenoid compound of formula (I) for use as herein described in the different embodiments above, wherein X is $CH_3$ and $R_1$ is H or $COC_nH_{2n+1}$ with n=7, 8, 9, 10, 11, 12, or 13. These microbial carotenoid compounds can also be defined herein as glycosyl-apo-8'-lycopene or $C_n$-glycosyl-apo-8'-lycopene with n selected from 8, 9, 10, 11, 12, 13 or 14.

In another preferred embodiment, the present invention relates to amicrobial carotenoid compound of formula (I) or a composition comprising a microbial carotenoid compound of formula (I) for use as herein described in the different wherein X is $COOCH_3$ and $R_1$ is H or $COC_nH_{2n+1}$ with n=5, 6, 7, 8, 9, 10 or 11. These microbial carotenoid compounds can also be defined as methyl-glycosyl-apo-8'-lycopenoate or methyl-$C_n$-glycosyl-apo-8'-lycopenoate with n selected 6, 7, 8, 9, 10, 11, or 12.

The microbial carotenoid compound or composition for use as herein described in all different embodiments, is further characterized in that the microbial carotenoid compound is derived from a bacterial species selected from *Bacillus, Staphylococcus, Streptococcus, Methylobacterium, Rubritalea* or *Sporosarcina*; more in particular, from a *Bacillus indicus* species. In an even further embodiment, the microbial carotenoid compound is derived from the PD01 strain, deposited under accession number LMG P-29664 (deposited at BCCM on Jun. 15, 2016) or the HU19 *Bacillus indicus* strain (with accession number NCIMB 41359).

As indicated above, the present invention is directed to at least one microbial carotenoid compound as defined herein above, a composition comprising said microbial carotenoid compound as defined herein above for use in restoring and/or maintaining a health-beneficial gut microbial composition in a subject. Said subject can be a mammal, a fish or a bird. In a particular embodiment, said subject is a human. In another particular embodiment, said subject is a production or farm animal or a pet. The production or farm animal can be selected from the group comprising a pig, a sheep, a goat, a cow, a horse, a chicken, a duck, a goose, a turkey, or a rabbit. The pet can be selected from a cat or a dog.

As already indicated herein above, the present invention discloses a carotenoid compound for use in restoring and/or maintaining a health-beneficial gut microbial composition in a subject. The gut microbial composition, or also called gut microbiota, is a complex ecosystem in the gastro-intestinal tract of a subject. It consists of the entire microbial community in the gut including bacteria, yeast, fungi, Archaea, and viruses. The gut microbiota maintains several essential functions, including colonic fermentation of dietary fibers, extraction of nutrients, synthesis of certain vitamins, prevention against colonization by pathogens, maturation of the intestinal epithelium and immune system, release of metabolites to the systemic tissues, and modulation of gastro-intestinal hormone release and nerve function. It is generally recognized that disturbance of the normal balance in the gut microbial composition can result in impaired intestinal barrier integrity and this is often observed in many different diseases. In the present invention, it is shown that the use of a carotenoid compound as defined herein above or a microbial material or a composition comprising said carotenoid compound results in restoring and/or maintaining a health-beneficial gut microbial composition in a subject. Said restoring and/or maintaining of a health-beneficial gut microbial composition includes:
    stimulation of the growth and/or activity of one or a limited number of beneficial bacteria in the intestinal tract,
    inhibition of the growth and/or activity of one or a limited number of pathogenic bacteria in the intestinal tract,
    increasing the attachment of non-pathogenic bacteria to the mucosa of the gastro-intestinal surface,
    reducing uncontrolled uptake of antigens, pro-inflammatory bacteria or bacterial products of the gut,
    providing anti-inflammatory activity at the intestinal surface,
    increasing gut barrier functions, and/or
    producing health-beneficial microbial metabolites.

In a further embodiment, the compound or composition according to the present invention as defined herein above is for use in the prevention and/or treatment of disorders associated with a disturbed intestinal barrier integrity. In a particular embodiment, said compound or composition is for use in the prevention and/or treatment of irritable bowel syndrome, inflammatory bowel disease, intestinal discomfort, diarrhoea, constipation, Crohn's disease, ulcerative colitis, coeliac disease, pouchitis, mucositis, gut infection by pathogens (bacteria, viruses, fungi), gut microbiota dysbiosis, metabolic syndrome, obesity, diabetes, chronic fatigue syndrome, a cardiovascular disease, a mental condition, a neurodegenerative disease, rheumatoid arthritis, spondyloarthritis, a form of cancer or any combination thereof. Examples of neurodegenerative diseases include, but are not limited to ALS, dementia, Alzheimer's, Parkinson's and Huntington's disease. Examples of types of cancers include, but are not limited to, lung cancer, breast cancer, prostate cancer, pancreatic cancer and particularly colorectal cancer. Examples of autoimmune diseases include, but are not limited to multiple sclerosis, atopic dermatitis, celiac disease, psoriasis and lupus.

In another embodiment, said compound or composition according to the present invention as defined herein above is for use in the prevention and/or treatment of increased plasma concentrations of pro-inflammatory cytokines in a subject, in particular in humans. Said increased plasma concentrations of pro-inflammatory cytokines in a subject, in particular in humans are observed in disorders selected from the group comprising irritable bowel syndrome, inflammatory bowel disease, Crohn's disease, ulcerative colitis, coeliac disease, pouchitis, mucositis, infectious diseases, rheumatism, rheumatoid arthritis, spondyloarthritis, hypercholesterolemia, metabolic syndrome, obesity, diabetes, an autoimmune condition, impaired immune function.

In yet another embodiment, the compound or composition according to the present invention as defined herein above is for use in the improvement of exercise performance.

In yet another embodiment, said compound or composition according to the present invention as defined herein above is for use in the improvement of gut maturation and gut barrier function in farm animals or fish. In an even further embodiment, said compound or composition is for use in the improvement of production parameters in farm animals or fish. Production parameters can include average daily gain (ADG) or feed conversion ratio (FCR) during the nursery and fattening phase. Further, production parameters are also reflected in the mortality in growing animals.

The present invention also discloses a method of treatment and/or prevention of a disorder associated with disturbed intestinal barrier integrity or a disorder associated with a disturbed gut microbial composition, wherein a carotenoid compound as defined herein above is used to stimulate growth and/or activity of one or a limited number of beneficial bacteria in the intestinal tract, to inhibit growth and/or activity of one or a limited number of pathogenic bacteria in the intestinal tract, to relatively increase the attachment of non-pathogenic bacteria to the mucosa of the gastro-intestinal surface, to reduce uncontrolled uptake of antigens, pro-inflammatory bacteria or bacterial products by the gut, to provide anti-inflammatory activity at the intestinal surface, to increase gut barrier functioning, and/or to produce health-beneficial microbial metabolites.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

DETAILED DESCRIPTION OF THE INVENTION

Figure 1:
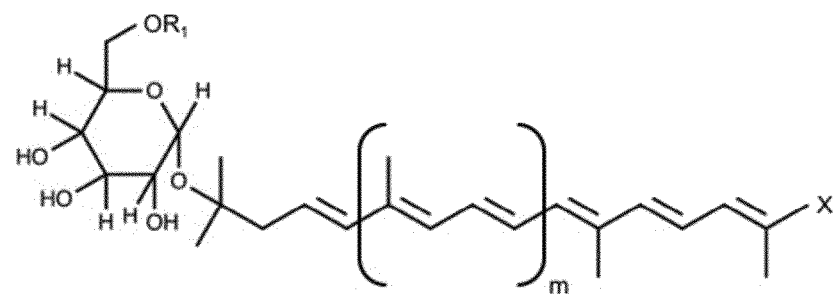
FIG. 1: Compound of formula (I).

The present invention relates to methods, compounds and compositions comprising microbial carotenoid compounds and their use, for modulating the gut microbial composition towards a more efficient and health-beneficial gut microbial community. In particular, the methods, compounds and compositions comprising microbial carotenoid compounds according to the present invention were found to have a beneficial effect on butyrate production in the intestine, primarily by modulating the gut microbiota towards an efficient butyrate-producing microbial community.

The gut microbial composition, or also called gut microbiome, is a complex ecosystem in the gastro-intestinal tract of a human or animal. It consists of the entire microbial community in the gut including bacteria, yeast, fungi, Archaea, and viruses. The gut microbiota maintains several essential functions, including colonic fermentation of dietary fibers, extraction of nutrients, synthesis of certain vitamins, prevention against colonization by pathogens, maturation of the intestinal epithelium and immune system, release of metabolites to the systemic tissues, and modulation of gastro-intestinal hormone release and nerve function. It is generally recognized that disturbance of the normal balance in the gut microbial composition can result in impaired intestinal barrier integrity and is observed in many different diseases, including irritable bowel syndrome, inflammatory bowel disease, intestinal discomfort, diarrhoea, constipation, Crohn's disease, ulcerative colitis, coeliac disease, pouchitis, mucositis, gut infection by pathogens (bacteria, viruses, fungi), gut microbiota dysbiosis, but also autoimmune diseases, metabolic syndrome, cardiovascular diseases, obesity, type 2 diabetes, chronic fatigue syndrome, a mental condition, a neurodegenerative disease, rheumatoid arthritis, spondyloarthritis, a form of cancer, or any combination thereof.

The gut microbiota is also a source of inflammatory molecules such as lipopolysaccharide and peptidoglycan that may contribute to metabolic disease.

The intestinal layer forms the final barrier between the luminal content and the host. Maintenance of this barrier is therefore extremely important and an impaired integrity of this intestinal layer is often the cause of many diseases, such as inflammatory bowel disease, irritable bowel syndrome or coeliac disease. The interaction between intestinal epithelial cells of the intestinal layer is therefore extremely important for maintaining the intestinal barrier integrity. These interactions are performed by tight junctions, desmosomes, adhesion junctions and gap junctions between the epithelial cells. Changes in the intestinal integrity may arise from changes in the mucus layer, changes in epithelial cell proliferation or cell death or changes in the connections, for example tight junctions, between adjacent cells.

Further, in the gut and during fermentation, anaerobic bacteria break down indigestible carbohydrates into short-chain fatty acids, including acetate, propionate and butyrate. Butyrate plays a key role in maintaining gut health as it is the major source of energy to the colonocytes, and as an important regulator of gene expression, inflammation, differentiation and apoptosis in host cells (Louis and Flint, FEMS Microbiol Lett 294, 2009). Further, butyrate plays an important role at the intestinal level by strengthening the epithelial defence barrier through its effect on mucus production and tight junction expression, resulting in a reduced passage of toxic and pro-inflammatory substances across the intestinal layer. Further, butyrate has been shown to decrease intestinal permeability in both in vitro and in vivo setups by limiting increased intestinal permeability induced in disease models. Further, butyrate administration to young animals, such as weaned piglets, stimulates body growth and feed intake, which is associated with improved maturation of the gastrointestinal tract.

In the present invention, it is shown that the a microbial carotenoid compound for use as defined herein above or a composition comprising said microbial carotenoid compound for use as defined herein above has a beneficial effect on butyrate production in the intestine, primarily by modulating the gut microbiota towards an efficient butyrate-producing microbial community. This beneficial effect was not observed using carotenoids of plant origin, for example lutein.

In one embodiment, the present invention therefore discloses a carotenoid compound of formula (I) for use in restoring and/or maintaining a health-beneficial gut microbial composition in a subject. As indicated herein above, in one embodiment of the invention, in formula (I) X is $CH_3$ or $COOR_2$ wherein $R_2$ is independently selected from methyl, ethyl, methylethyl, propyl, isopropyl, butyl, isobutyl, sec-butyl and tert-butyl, and wherein m is selected from 0, 1, 2 or 3, and wherein $R_1$ is H or $COC_nH_{2n+1}$ with n is selected from 5, 6, 7, 8, 9, 10, 11, 12, 13 or 14. Preferred carotenoid compounds of the invention are those of Formula (I) as shown in FIG. 1 wherein X is $CH_3$ or $COOCH_3$, and wherein m is 3, and wherein $R_1$ is H or $COC_nH_{2n+1}$ with n is selected from 5, 6, 7, 8, 9, 10, 11, 12, or 13. Preferably, X is $CH_3$ and $R_1$ is H or $COC_nH_{2n+1}$ with n being selected from 7, 8, 9, 10, 11, 12 or 13. In another preferred embodiment, X is $COOCH_3$ and $R_1$ is H or $COC_nH_{2n+1}$ with n being selected from 5, 6, 7, 8, 9, 10, or 11. In a further preferred embodiment, these microbial carotenoid compounds are glycosyl-apo-8'-lycopene or $C_n$-glycosyl-apo-8'-lycopene with n being selected from 8, 9, 10, 11, 12, 13 or 14. In another preferred embodiment, these microbial carotenoid compounds are methyl-glycosyl-apo-8'-lycopenoate or methyl-$C_n$-glycosyl-apo-8'-lycopenoate with n being selected from 6, 7, 8, 9, 10, 11, or 12.

The microbial carotenoid compound of the present invention belongs to the group of carotenoids. Carotenoids have recently gained a lot of interest in the functional food industry due to their potential health benefits. Originally found in plants, serving as an accessory pigment during photosynthesis, carotenoids are lipophilic anti-oxidants that have been linked to a decreased risk of cardiovascular disease, macular degeneration and other chronic diseases. While carotenoid production has also been found in some bacteria and fungi for protection against UV damage and oxidative stress, humans and other animals are unable to synthesize carotenoids, and therefore need to obtain them from their diet. The absorption of carotenoids from the diet depends upon efficient release of the carotenoids from the food matrix and subsequent solubilisation by bile acids and digestive enzymes, culminating in their incorporation into mixed micelles. The main part of carotenoid metabolism occurs in the small intestine where they must also be dissolved in dietary lipids before they can passively migrate from the micellar phase through the lumen of the intestine to the lymphatic and blood circulatory system. It is however unknown whether all the carotenoids present in a mixed micelle are absorbed, or whether some are left behind in association with unabsorbed bile salts and cholesterol to be absorbed more distally or lost to the large intestine where they can exert other biological functions.

More than 600 naturally occurring carotenoids have been identified, of which approximately 50 can be converted into retinol (i.e. Vitamin A), and are referred to as provitamin A carotenoids. Provitamin A carotenoids can be converted enzymatically in the intestinal mucosa to yield retinol. Retinol is required for vision, maintenance of differentiated epithelia, mucus secretion and reproduction (McCullough et al., 1999, Proc Nutr Society, 58(2)). In humans, provitamin A activity is the only function of carotenoids that is firmly recognized and linked to health outputs. In addition to their provitamin A activity, many carotenoids have been considered to have many biological functions such as the inhibition of lipid peroxidation, tumor-suppressive activity, immuno-modulation, etc. which are mostly related to their anti-oxidant properties. Cancer-preventive activities of carotenoids have been associated with their anti-oxidant properties and the induction and stimulation of intercellular communication via gap junctions which apply a role in the regulation of cell growth, differentiation and apoptosis. Gap junctional communication between cells appears to be independent of their anti-oxidant property or provitamin A activity (Zhang et al., 1992, Cancer Res 52). Additionally, Vieira et al. (2008, J Pediatr Gastroenterol Nutr 47) have shown that serum concentrations of carotenoids are correlated with gut barrier integrity. Carotenoids may therefore provide a good marker for disrupted intestinal barrier function.

The microbial carotenoid compound for use according to the present invention can be derived from bacterial spores, vegetative bacterial cells, extracts of bacterial cells, metabolites of bacterial cells or any combination thereof from a bacterial species selected from *Bacillus, Staphylococcus, Streptococcus, Methylobacterium, Rubritalea* or *Sporosarcina*. In a particularly preferred embodiment, said the carotenoid compound for use according to the different embodiments of the present invention is derived from the *Bacillus indicus* species. In a further preferred embodiment, said carotenoid compound is derived from the *Bacillus*

*indicus* PD01 strain deposited under accession number LMG P-29664 (deposited at BCCM on Jun. 15, 2016) or the *Bacillus indicus* HU19 strain (with accession number NCIMB 41359).

Bacteria are typically in the form of bacterial spores or as vegetative bacterial cells, or a mixture of both. In a particularly preferred instance, the bacteria are in the form of bacterial spores, they may have been treated such that they cannot germinate. For example, the spores could be treated by heat and may, for instance, have been subjected to autoclaving to prevent germination. In many instances the bacteria may be provided in the form of spores which can germinate. In another preferred embodiment, the bacteria are in the form of vegetative cells. The spores or vegetative cells may, in one embodiment, be provided in isolated form. In yet another embodiment, the microbial material can be extracts of bacterial cells. In still another embodiment, the microbial material can be metabolites of bacterial cells released during cell growth in the culture medium. In another further embodiment, the microbial material can be any combination of bacterial spores, vegetative bacterial cells, extract of bacterial cells or metabolites of bacterial cells.

The microbial carotenoid compound for use according to the different embodiments of the present invention results in an increased butyrate production by the gut microbiota. In particular, said microbial carotenoid compound modulates the gut microbial composition in favour of butyrate-producing bacteria. Expressed differently, the microbial carotenoid compound for use according to the present invention results in restoring and/or maintaining a health-beneficial gut microbial composition by inducing changes in the gut microbial composition in favour of butyrate-producing bacteria. Further, the microbial carotenoid compound for use according to the present invention also improves the gut barrier function by reducing the gut barrier permeability and increasing the gut barrier resistance.

As used herein, the carotenoid compound, a microbial material or a composition as defined herein above is for use in restoring and/or maintaining a health-beneficial gut microbial composition in a subject. Said restoring and/or maintaining of a health-beneficial gut microbial composition includes:
  stimulation of the growth and/or activity of one or a limited number of beneficial bacteria in the intestinal tract,
  inhibition of the growth and/or activity of one or a limited number of pathogenic bacteria in the intestinal tract,
  increasing the attachment of non-pathogenic bacteria to the mucosa of the gastro-intestinal surface,
  reducing uncontrolled uptake of antigens, pro-inflammatory bacteria or bacterial products of the gut,
  providing anti-inflammatory activity at the intestinal surface,
  increasing gut barrier functions, and/or
  producing health-beneficial microbial metabolites.

Expressed differently, the carotenoid compound, microbial material or a composition according to the present invention is for use in restoring and/or maintaining the normal homeostasis in the gut microbial composition in a subject, and therefore also results in restoring and/or maintaining the general gut health in a subject.

Because of its positive effects on the intestinal barrier function, the present invention is also directed to a microbial carotenoid compound of formula (I) and as defined herein above or a composition comprising said compound for use in the prevention and/or treatment of disorders associated with a disturbed intestinal barrier integrity. Further, the present invention also discloses a method of treatment and/or prevention of a disorder associated with disturbed intestinal barrier integrity wherein a compound or composition according to this invention and as defined herein above is used to:
  stimulation of the growth and/or activity of one or a limited number of beneficial bacteria in the intestinal tract,
  inhibition of the growth and/or activity of one or a limited number of pathogenic bacteria in the intestinal tract,
  increasing the attachment of non-pathogenic bacteria to the mucosa of the gastro-intestinal surface,
  reducing uncontrolled uptake of antigens, pro-inflammatory bacteria or bacterial products of the gut,
  providing anti-inflammatory activity at the intestinal surface,
  increasing gut barrier functions, and/or
  producing health-beneficial microbial metabolites.

Disorders associated with a disturbed intestinal barrier integrity or associated with intestinal barrier dysfunction are selected from, but not limited to, the group comprising irritable bowel syndrome, inflammatory bowel disease, intestinal discomfort, diarrhoea, constipation, Crohn's disease, ulcerative colitis, coeliac disease, pouchitis, mucositis, gut infection by pathogens (bacteria, viruses, fungi), gut microbiota dysbiosis, metabolic syndrome, obesity, diabetes, chronic fatigue syndrome, a cardiovascular disease, a mental condition, a neurodegenerative disease, rheumatoid arthritis, spondyloarthritis, a form of cancer or any combination thereof.

'Inflammatory bowel disease' (IBD), also referred to as 'chronic colonic disease', as used herein includes any condition characterized by persistent mucosal inflammation at different levels of the gastrointestinal tract, such as for example Crohn's disease or ulcerative colitis.

'Irritable bowel syndrome' (IBS) as used herein is a common disorder that affects the large intestine or colon. IBS commonly causes cramping, abdominal pain, bloating, gas, diarrhoea, and constipation. In contrast to other gastrointestinal diseases like Crohn's disease or ulcerative colitis, IBS is a chronic condition that does not cause changes in bowel tissue or increases the risk of colorectal cancer. In a diarrhoea-predominant IBS, electron microscopy studies showed cytoskeleton condensation and enlarged intercellular spaces between epithelial cells, providing the morphological basis for increased intestinal permeability in IBS.

'Ulcerative colitis' as used herein is a chronic relapsing form of IBD that causes inflammation and ulcers in the colon. The disease is a type of colitis, which is a group of diseases that cause inflammation of the colon. The hallmark symptom of active ulcerative colitis is diarrhoea mixed with blood.

'Crohn's disease' is also a type of IBD that may affect any part of the gastrointestinal tract from mouth to anus. Signs and symptoms often include abdominal pain, diarrhoea, which may be bloodly, fever, and weight loss. Other complications may occur outside the gastrointestinal tract and include anaemia, skin rashes, arthritis, inflammation of the eye, and feeling tired. Bowel obstruction also commonly occurs and those with the disease are at greater risk of bowel cancer.

Crohn's disease is caused by a combination of environmental, immune and bacterial factors in genetically susceptible individuals. It results in a chronic inflammatory disorder, in which the body's immune system attacks the gastrointestinal tract possibly directed at microbial antigens.

As used herein, 'pouchitis' is defined as inflammation of the ileal pouch. An ileal pouch is an artificial rectum surgically created out of ileal gut tissue in patients who have undergone a colectomy. An ileal pouch is often created in the management of patients with ulcerative colitis.

'Coeliac disease' is an autoimmune disorder affecting primarily the small intestine. Classic symptoms include gastrointestinal problems such as chronic diarrhoea, abdominal distention, malabsorption, loss of appetite, and among children failure to grow normally. The disease is caused by a reaction to gluten. Upon exposure to gluten, an abnormal immune response may lead to the production of several different autoantibodies that can affect a number of different organs. In the small intestine, this causes an inflammatory reaction and may produce shortening of the villi lining the small intestine, resulting in a disturbed absorbance of nutrients, frequently leading to anaemia.

Examples of neurodegenerative diseases include, but are not limited to ALS, dementia, Alzheimer's, Parkinson's and Huntington's disease. Examples of types of cancers include, but are not limited to, lung cancer, breast cancer, prostate cancer, pancreatic cancer and particularly colorectal cancer. Examples of autoimmune diseases include, but are not limited to multiple sclerosis, atopic dermatitis, celiac disease, psoriasis and lupus.

The present invention is also directed to a microbial carotenoid compound of formula (I) and as defined herein above or a composition comprising said compound for use in the prevention and/or treatment of increased plasma concentrations of pro-inflammatory cytokines in humans. Disorders with increased plasma concentrations of pro-inflammatory cytokines in humans can be selected from, but are not limited to, the group comprising irritable bowel syndrome, inflammatory bowel disease, Crohn's disease, ulcerative colitis, coeliac disease, pouchitis, mucositis, infectious diseases, rheumatism, rheumatoid arthritis, spondyloarthritis, hypercholesterolemia, metabolic syndrome, obesity, diabetes, autoimmune diseases, or impaired immune function.

In yet another embodiment, the compound or composition according to the present invention as defined herein above is for use in the improvement of exercise performance. Athletes exposed to high-intensity exercise show an increased occurrence of gastrointestinal symptoms like cramps, diarrhoea, bloating, nausea, and bleeding. These symptoms have been associated with alterations in intestinal permeability and decreased gut barrier function. The increased gastrointestinal permeability also leads to endotoxemia, and results in increased susceptibility to infectious and autoimmune diseases, due to absorption of pathogens or toxins into tissue and the bloodstream.

The present invention also provides a microbial carotenoid compound as defined herein above, or a composition comprising said compound for use in the improvement of gut maturation and gut barrier function in farm animals or fish. In particular, the microbial carotenoid compound or compositions according to the present invention improves the general gut health in animals, such as farm animals or fish, by enhancing the gut barrier function and modulating the gut microbiota composition, thereby improving gut maturation.

It is generally known that the overall performance and production of animals, in particular pigs, livestock or fish, is related to the general health status of the animals. Prevention of infections, and warranty of a healthy status in the animals are therefore crucial for the meat industry or fish aquaculture. Both in the meat industry as in the fish aquaculture, production parameters are crucial to measure the productivity of a farm animal or fish aquaculture. For farm animals, such as pigs, sheep, cattle, horses, or poultry, these parameters include average daily gain (ADG) or feed conversion ratio (FCR) during the nursery and fattening phase. In addition, production parameters are also reflected in the mortality in growing animals.

EXAMPLES

The invention is further described by reference to the following experimental examples. These examples are provided for purpose of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using these preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Characterization of Carotenoids Extracted from *Bacillus indicus* Strain PD01 (LMG P-29664)

Figure 2:
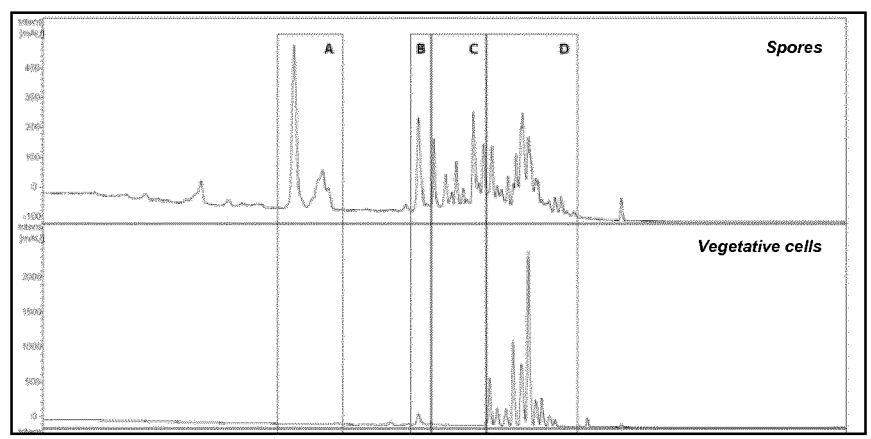
FIG. 2: Profile of carotenoids contained within *Bacillus indicus* strain PD01 vegetative cells and spores. A=non-esterified orange carotenoids, B=non-esterified yellow carotenoids, C=esterified orange carotenoids, D=esterified yellow carotenoids.

Carotenoids from PD01 (LMG P-29664), either derived from vegetative cells or spores, were characterized by ultra-high performance liquid chromatography-diode array detection-mass spectrometry (UHPLC-DAD-MS). The carotenoids were extracted from the bacteria by an optimized lipid extraction and their carotenoid composition and content was determined by HPLC analysis on a C18 column. Results showed that the extracts from vegetative cells were mainly composed of carotenoids which absorb at 430/454/484 nm and these carotenoids were defined as esterified and non-esterified yellow carotenoids (FIG. 2). In contrast, the extracts produced from spores were composed of two groups of carotenoids which absorb at 430/454/484 nm (yellow carotenoids) and at 440/466/494. The latter were defined as esterified and non-esterified orange carotenoids (FIG. 2).

Figure 3:
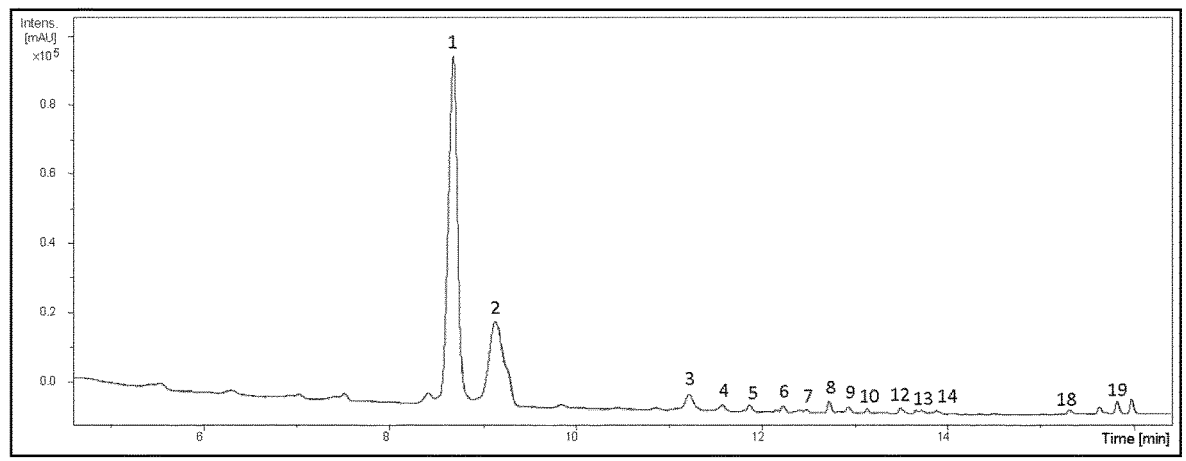
FIG. 3: Carotenoid profile of "Free O" carotenoid extract of *Bacillus indicus* strain PD01. The chromatogram is extracted at 200-600 nm.

Two different carotenoid extracts from PD01 were further analyzed by UHPLC-DAD-MS and spectrophotometry in order to identify the different individual carotenoids present in the mixture. The first carotenoid extract, called "Free O" (for "Free Orange") extract, was obtained from a mixture of vegetative cells and spores. The major carotenoid present in the extract was the orange carotenoid methyl-glycosyl-apo-8'-lycopenoate (as the free form, FIG. 3, peaks 1 & 2) and the other carotenoids found in lesser amounts in this extract were the esterified forms of this orange carotenoid (FIG. 3, peaks 4-10), and the free and esterified forms of the yellow carotenoid (FIG. 3, peaks 3 and 12-14) as well as 8'-apo-phytoene (peak 18, precursor of orange/yellow carotenoid) and menaquinone-7 (FIG. 3, peak 19). Spectral properties and specific identification of these carotenoids can be found in Table 1.

Figure 4:
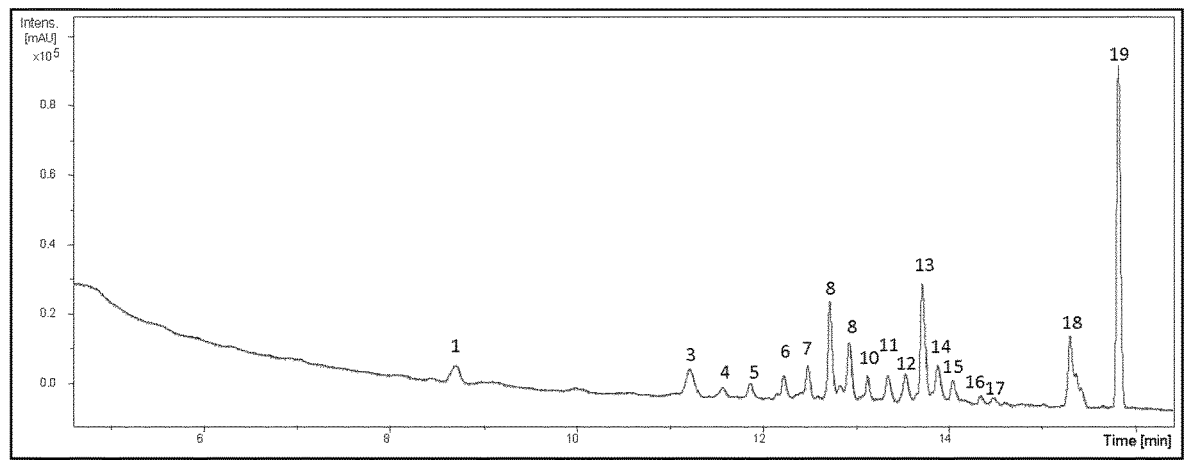
FIG. 4: Carotenoid profile of "Ester Y/O" carotenoid extract of Bacillus indicus strain PD01. The chromatogram is extracted at 200-600 nm.

Another extract of the PD01 strain, called "Ester Y/O" (for "Ester Yellow/Orange") extract, was obtained from another mixture of vegetative cells and spores (different ratio). UHPLC-DAD-MS analysis revealed that this extract was mainly composed of the esterified form of orange carotenoids and the esterified form of yellow carotenoids (FIG. 4, peaks 4-17). In this extract, the content of menaquinone-7 (peak 19) and of 8'-apophytoene (peak 18, precursor of orange/yellow carotenoid) was significant. The identification and spectral properties of different peaks are detailed in Table 1.

TABLE 1

Spectral properties and identification of PD01 carotenoids.

| Peak | Carotenoids | λ max (nm) | m/z [M + H]$^+$ | Color |
|------|-------------|------------|-----------------|-------|
| 1 | methyl-glycosyl-apo-8'-lycopenoate | 440/466/494 | 625.3 | Orange |
| 2 | cis-methyl-glycosyl-apo-8'-lycopenoate | 440/466/494 | 625.3 | Orange |
| 3 | glycosyl-apo-8'-lycopène | 430/454/484 | 581.3 | Yellow |
| 4 | methyl-C6-glycosyl-apo-8'-lycopenoate | 440/466/494 | 723.5 | Orange |
| 5 | methyl-C7-glycosyl-apo-8'-lycopenoate | 440/466/494 | 737.5 | Orange |
| 6 | methyl-C8-glycosyl-apo-8'-lycopenoate | 440/466/494 | 751.6 | Orange |
| 7 | methyl-C9-glycosyl-apo-8'-lycopenoate | 440/466/494 | 765.6 | Orange |
| 8 | methyl-C10-glycosyl-apo-8'-lycopenoate | 440/466/494 | 779.6 | Orange |
| 9 | methyl-C11-glycosyl-apo-8'-lycopenoate | 440/466/494 | 793.7 | Orange |
| 10 | methyl-C12-glycosyl-apo-8'-lycopenoate | 440/466/494 | 807.6 | Orange |
| 11 | C8-glycosyl-apo-8'-lycopène | 430/454/484 | 707.6 | Yellow |
| 12 | C9-glycosyl-apo-8'-lycopène | 430/454/484 | 721.6 | Yellow |
| 13 | C10-glycosyl-apo-8'-lycopène | 430/454/484 | 735.7 | Yellow |
| 14 | C11-glycosyl-apo-8'-lycopène | 430/454/484 | 749.6 | Yellow |
| 15 | C12-glycosyl-apo-8'-lycopène | 430/454/484 | 763.5 | Yellow |
| 16 | C13-glycosyl-apo-8'-lycopène | 430/454/484 | 791.5 | Yellow |
| 17 | C14-glycosyl-apo-8'-lycopène | 430/454/484 | 805.5 | Yellow |
| 18 | 8'-apophytoene | 276/287/298 | 409.3 | — |
| 19 | menaquinone-7 | 262/270/330 | 649.7 | — |

Example 2

Effect of Carotenoids from Strain PD01 (LMG P-29664) on Butyrate Production In Vitro To study the effect of repeated ingestion of the carotenoids from strain PD01 on butyrate production, experiments were conducted with a dynamic gut model, the Simulator of the Human Intestinal Microbial Ecosystem (SHIME®). During the experiments, SHIME units consisted of three consecutive vessels representing the stomach/small intestine, the proximal colon and the distal colon, respectively. To address different formulations of the carotenoids (i.e. carotenoids extracted from bacterial cells ("CAR") or contained within (vegetative) bacterial cells ("VEG")), identical SHIME units were run in parallel. Upon a 2-week stabilization period, a reference control period was implemented (2 weeks), after which the carotenoids were daily administered for 3 weeks during the treatment period. Carotenoids were either administered as extract or as vegetative cells at similar carotenoid levels. While the carotenoid extract was administered to the stomach compartment, as they can withstand the harsh gastric conditions, gastric-sensitive vegetative cells were administered at the beginning of the small intestinal incubation, as this simulates the targeted delivery strategy using gastric-protective capsules.

Short-chain fatty acid (SCFA) production was monitored as a marker of saccharolytic fermentation. The specific production of certain SCFA is related with various health effects. Acetate can be used as energy source for the host. Propionate reduces cholesterol and fatty acid synthesis in the liver. Butyrate is a major energy source for colonocytes and induces differentiation in these cells.

Figure 5:
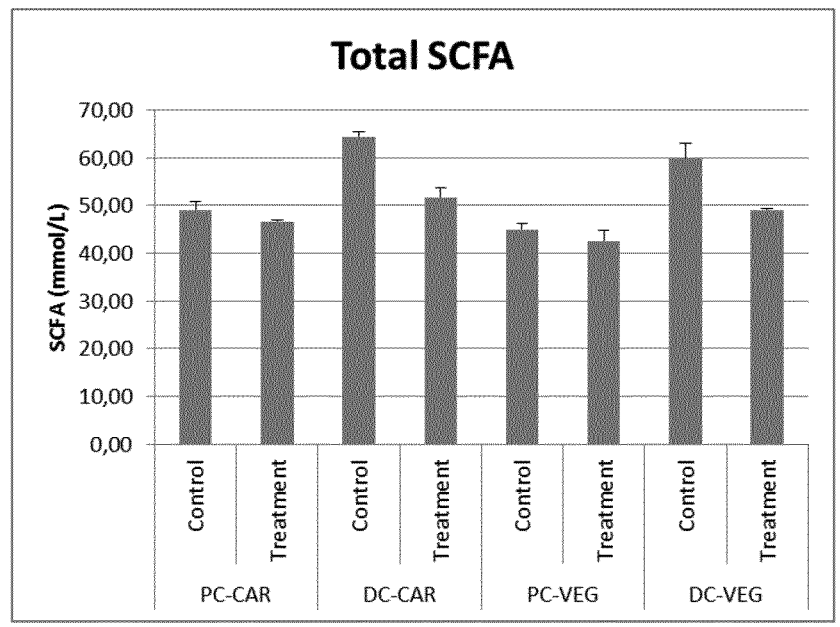
FIG. 5: Total short-chain fatty acid (SCFA) levels (mM) (A) and butyrate over acetate (B/A) ratio (B) measured in the proximal colon (PC) or the distal colon (DC) compartment of a Simulator of the Human Intestinal Microbial Ecosystem (SHIME®) either untreated (control) or treated with carotenoids extracted from strain PD01 (CAR) or carotenoids contained within vegetative cells of strain PD01 (VEG).
Figure 5:
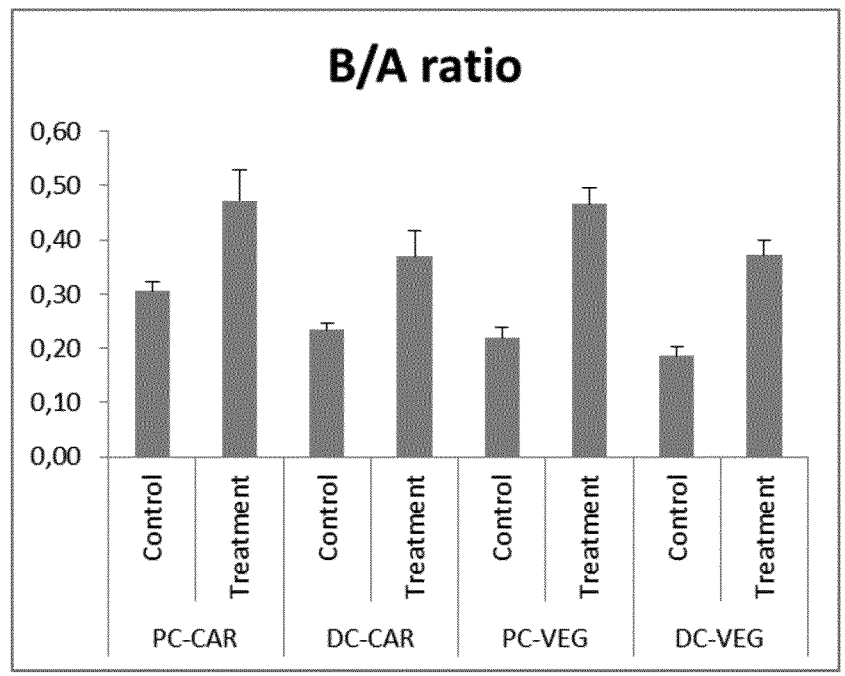

The results from a SHIME experiment showed that while no or minor changes in the total SCFA production were reported (FIG. 5A), both free carotenoids and carotenoids administered as vegetative cells altered the SCFA profiles by inducing a shift from acetate to the health-promoting SOFA butyrate (FIG. 5B). For further confirmation, another experiment was set up with the same design, yet in which the carotenoids were administered as bacterial spores. Again, administration of the spores resulted in an increase in butyrate over acetate ratio.

Therefore, it can be concluded that administration of carotenoids from PD01 (administered either as free carotenoids or contained within the bacterial cells/spores) has a beneficial effect on the microbial community activity.

Example 3

Effect of Carotenoids from Strain PD01 (LMG P-29664) on Gut Microbiome Composition In Vitro To study the effect of repeated ingestion of the carotenoids from strain PD01 on gut microbiome composition, experiments with the dynamic gut model SHIME®, were conducted. Experimental details are described in example 2.

QPCR and DGGE profiles were prepared to investigate whether strain PD01 might affect the microbial community composition. qPCR has been used to monitor specific bacterial groups, namely Firmicutes, Bacteroidetes, *Bifidobacterium, Lactobacillus* and *Clostridium coccoides/Eubacterium rectale* group, while DGGE profiles were generated from the total microbial community. Firmicutes and Bacteroidetes are the 2 most dominant bacterial phyla in the human gut. Bacteroidetes are considered as very important saccharolytic fermenting bacteria, as a large part of the proteins of Bacteroidetes goes to breaking down polysaccharides and metabolizing their sugars. Some species belonging to this group are also associated with propionate production. Firmicutes are rather users of the metabolic intermediates produced by the metabolism of Bacteroidetes. They include several butyrate producers (including *Clostridium coccoides* and *Eubacterium rectale*), a bacterial metabolite considered as health-beneficial. *Bifidobacteria* and *Lactobacilli* are 2 bacterial genera known for their health-promoting properties.

Figure 6:
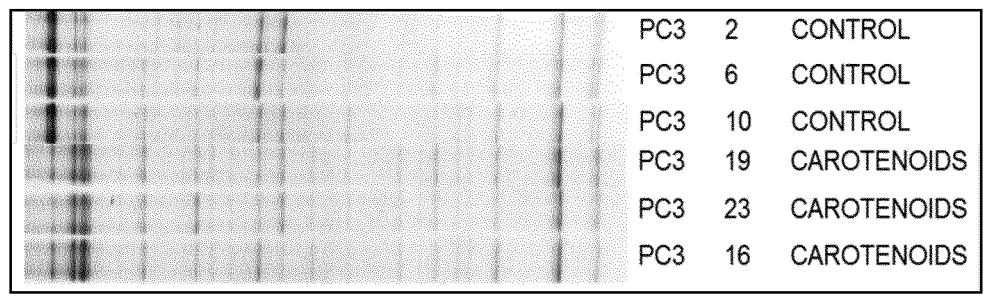
FIG. 6: Denaturing gradient gel electrophoresis (DGGE) profile upon treatment of the proximal colon (PC) (A) or the distal colon (DC) (B) compartment of the SHIME experiment with carotenoids extracted from strain PD01.
Figure 6:
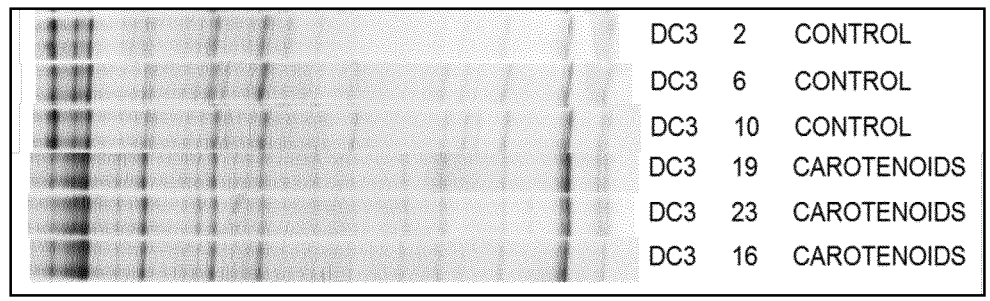
Figure 7:
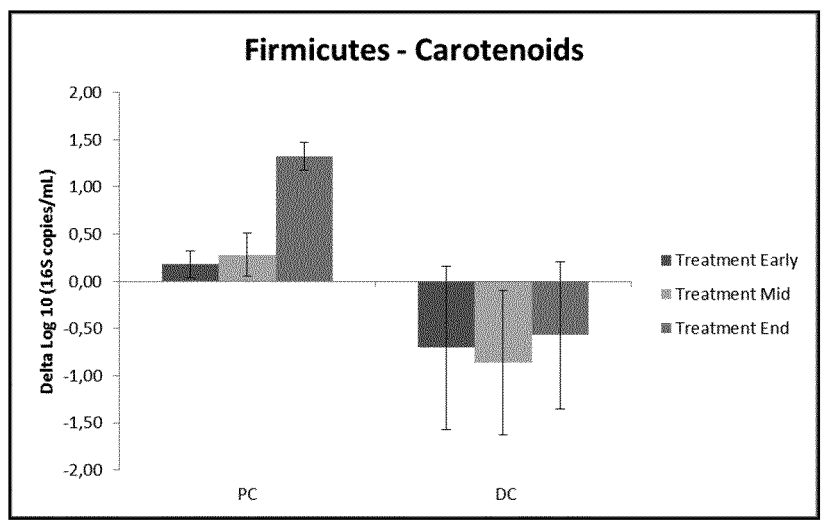
FIG. 7: qPCR results from the Firmicutes (A) and Clostridium coccoides/Eubacterium rectale (B) group upon treatment of the proximal colon (PC) and distal colon (DC) compartment of a SHIME treated with carotenoid extracted from strain PD01. Results are expressed as increase/decrease in abundance as compared to the control period.
Figure 7:
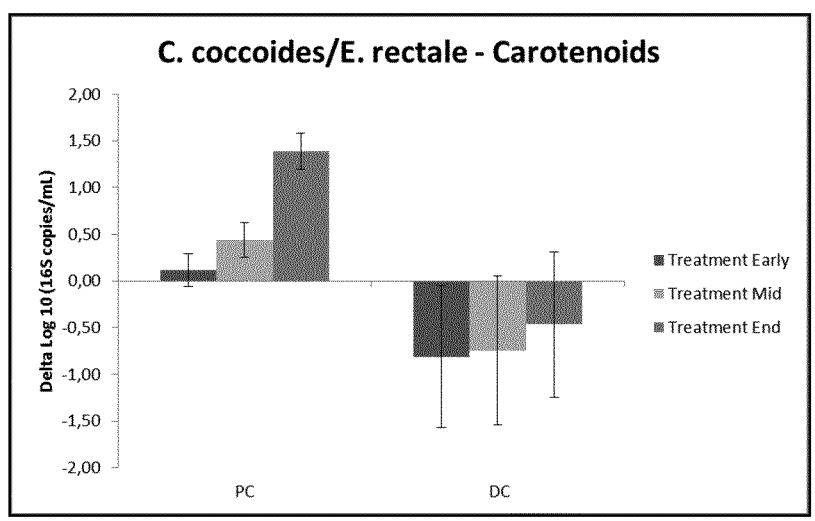

The DGGE profiles from a SHIME experiment conducted with carotenoids extracted from bacterial cells showed drastic changes in the composition of the gut microbial community (FIG. 6). The findings from the DGGE profiles were confirmed with qPCR. Indeed, treatment with carotenoids extracted from PD01 increased the concentrations of all bacterial groups tested, mainly in the proximal colon. The most interesting results were observed within the Firmicutes and the *Clostridium coccoides/Eubacterium rectale* group (FIG. 7). As the Firmicutes include several butyrate producers (including *Clostridium coccoides* and *Eubacterium rectale*), the increased concentrations can be considered as health-beneficial.

Figure 8:
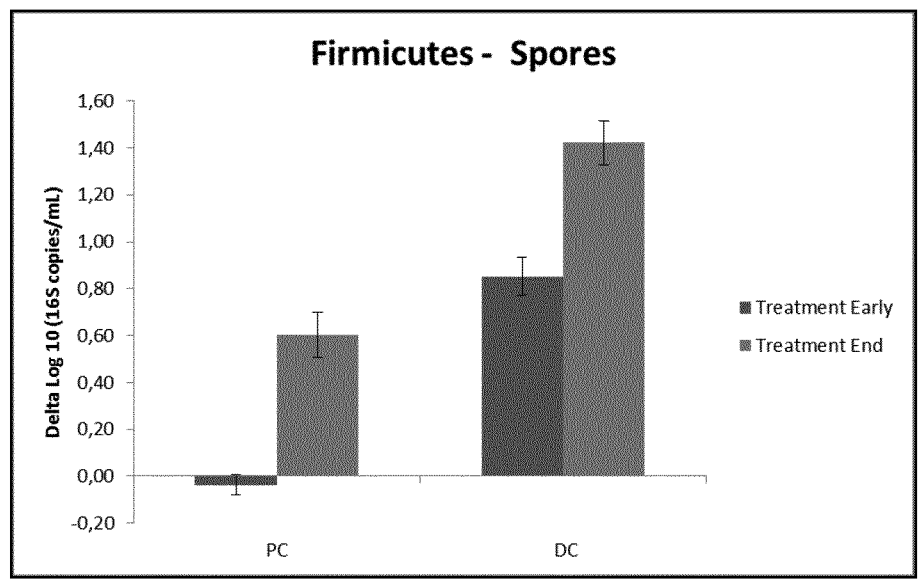
FIG. 8: qPCR results from the Firmicutes (A) and Clostridium coccoides/Eubacterium rectale (B) group upon treatment of the proximal colon (PC) and distal colon (DC) compartment of a SHIME treated with carotenoids contained within strain PD01spores. Results are expressed as the increase/decrease in abundance as compared to the control period.
Figure 8:
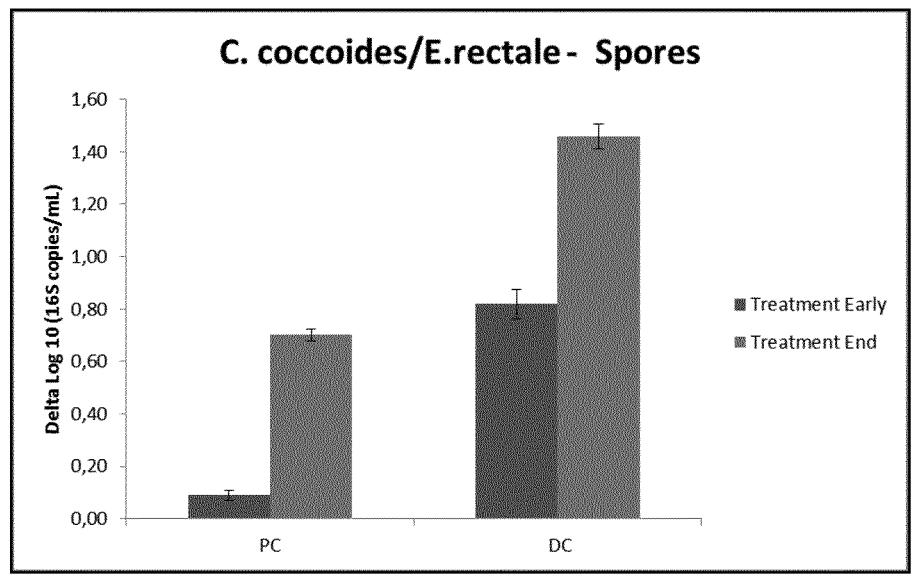

QPCR profiles from a SHIME experiment conducted with carotenoids contained within bacterial spores confirmed these results. Indeed, administration of bacterial spores again resulted in increased concentrations of the main bacterial groups tested, especially the Firmicutes and *Clostridium coccoides/Eubacterium rectale* group (FIG. 8).

This experiment therefore confirms that carotenoids from PD01 affect gut microbiome composition and specifically stimulate butyrate-producing bacterial groups.

Example 4

Effect of Carotenoids from Strain PD01 (LMG P-29664) on Gut Microbiome Composition In Vivo To evaluate the effect of carotenoids from PD01 on gut microbiome composition in vivo, male Sprague-Dawley rats of 90 days of age were daily dosed for 8 weeks with carotenoids from PD01, either as carotenoid extract or as carotenoids contained in spores or vegetative cells. The experiment consisted of administration of a high-fat (HF) diet to the animals, which mimics a standardized western diet and is associated with the development of metabolic syndrome within 8 weeks of administration. In addition to a HF control group, separate groups of animals received the HF diet in combination with one of the carotenoid formulations from PD01. To do this, the carotenoid formulations were suspended in peanut oil and given by oral gavage to the rats in addition to the HF diet. The corresponding daily dose of carotenoids was in the range of 10-50 pg/d.

A control group receiving a standard low-fat (LF) diet was included to allow assessment of the specific effect of the HF diet on the gut microbiome composition. Additionally, one extra HF group was included, receiving the plant-derived carotenoid lutein, in the same amount as the bacterial carotenoids (i.e. 25 µg/d). This allows comparison of the effect of bacterial vs. plant-derived carotenoids on the gut microbiome composition.

To monitor the effects of the different formulations on the gut microbiota, DGGE profiles were prepared. The total DNA of the fecal samples from the long-term in vivo experiment was extracted, and used as a template in nested PCR reactions to amplify the V4-V6 hypervariable region of the bacterial 16S rDNA-gene.

Figure 9:
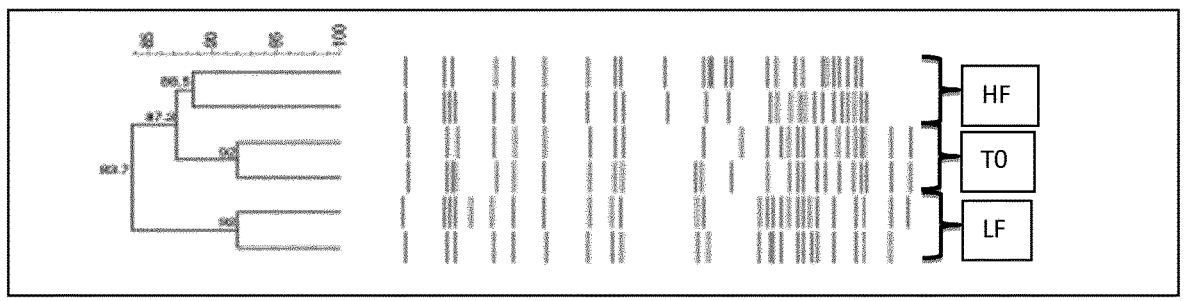
FIG. 9: Dendrogram, comparing the gut microbiota of rats before treatment (T0), rats treated for 8 weeks with a low-fat diet (LF) and rats treated for 8 weeks with a high-fat diet (HF).
Figure 10:
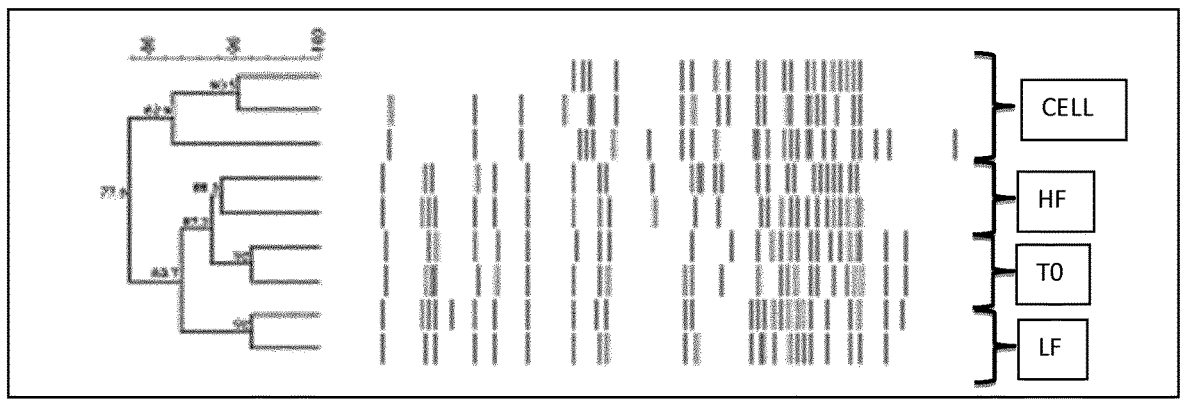
FIG. 10: Dendrogram, comparing the gut microbiota of rats before treatment (T0), rats treated for 8 weeks with a low-fat diet (LF), rats treated for 8 weeks with a high-fat diet (HF), rats treated for 8 weeks with a high-fat diet and carotenoids contained within strain PD01 vegetative cells.
Figure 11:
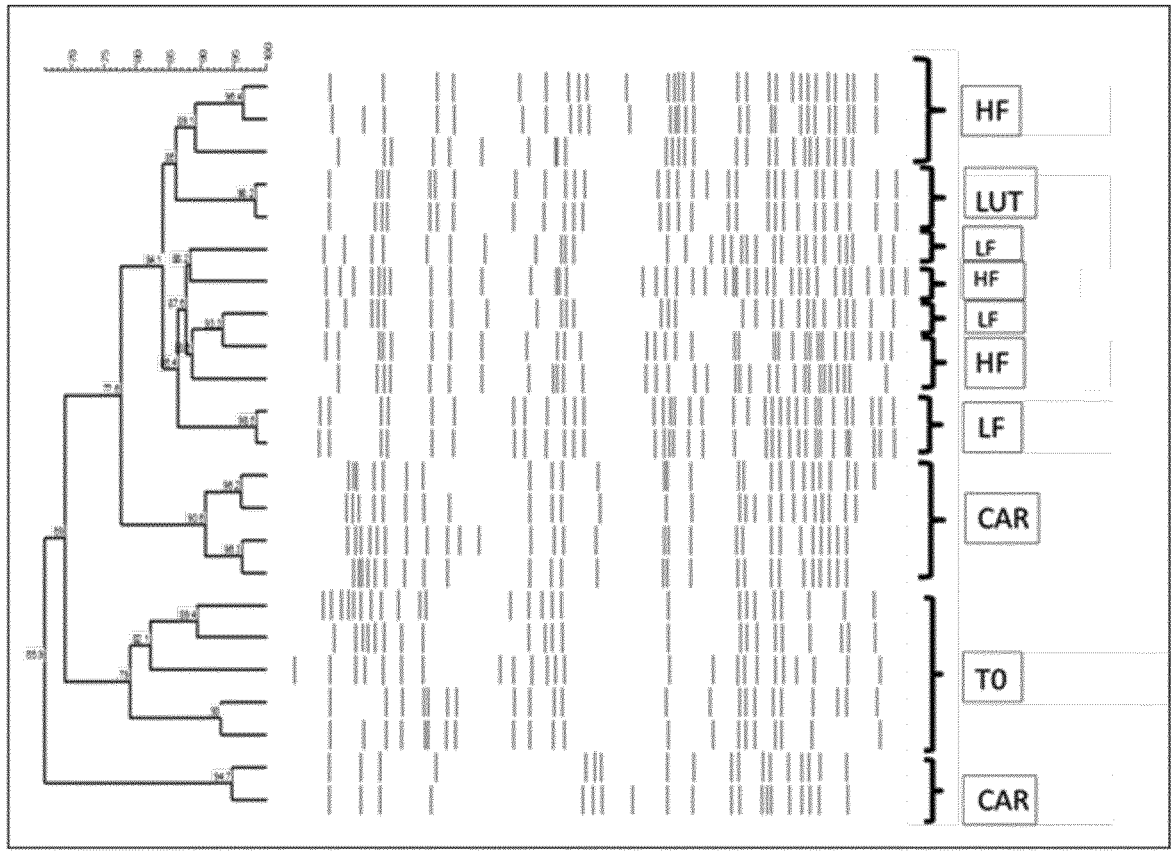
FIG. 11: Dendrogram, comparing rats before treatment (T0), rats treated for 8 weeks with a low-fat diet (LF), rats treated for 8 weeks with a high-fat diet (HF), rats treated for 8 weeks with a high-fat diet and lutein (LUT), and rats treated for 8 weeks with a high-fat diet and carotenoids extracted from strain PD01 (CAR).

A detailed cluster analysis of the various groups showed that after 8 weeks of treatment the gut microbiota of rats receiving a LF or a HF differed from each other and both differed from the gut microbiota of the rats before treatment (FIG. 9). This indicates that changing the diet has partially altered the microbial composition of the gut. However, treatment with carotenoids from PD01 had a strong additional effect on the gut microbiome composition, as shown in the example of the cluster analysis including the microbiome profiles of rats treated with carotenoids contained within PD01 vegetative cells (FIG. 10) or treated with carotenoids extracted from PD01 (FIG. 11). The same results were obtained upon dosing carotenoids contained within PD01 spores, confirming that carotenoids from PD01 additionally modified the gut microbiome of rats on a high-fat diet, irrespective of the carotenoid formulation used.

Interestingly, the gut microbial composition profiles of the rats treated with lutein clustered together with those of the HF controls, which indicates that animals within these groups were similar in terms of gut microbial composition. In contrast, the gut microbial composition of the rats treated with carotenoids extracted from PD01 was strongly different (FIG. 11). This surprising effect shows that microbial carotenoids alter the effect of a high-fat diet on the gut microbial composition while the plant-derived carotenoid does not have these properties.

Example 5

Effect of Carotenoids from Strain PD01 (LMG P-29664) on Gut Barrier Function In Vitro The effect on the host of the carotenoids from PD01 (derived from either vegetative cells or spores) on gut barrier function, was studied in Caco-2/THP1XB co-cultures, according to methods described in Possemiers et al. (2013, J Agric Food Chem 61). Endpoint of the measurement was a change from control in the transepithelial electrical resistance (TEER) in a transwell setup.

Figure 12:
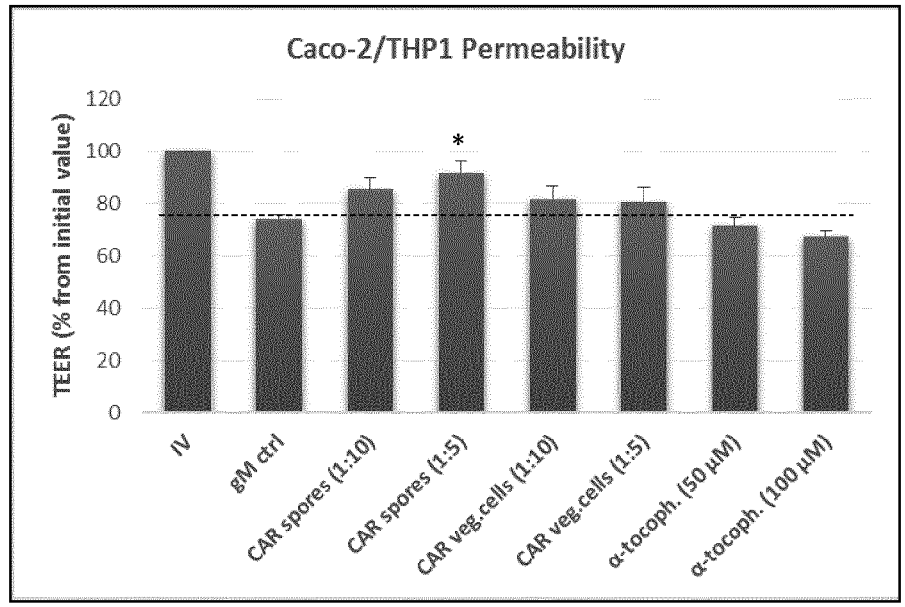
FIG. 12: Transepithelial electrical resistance (TEER) measured 18 h after treatment of the Caco-2/THP1XB co-cultures with carotenoids extracted from or contained within vegetative cells or spores of strain PD01. The dotted line is set to the gM control average for comparison purposes. (*) represents significantly different from gM control (t-test);. α-tocoph.=alpha-tocopherol; CAR=carotenoids extracted from strain PD01s; CELL, carotenoids contained within strain PD01 vegetative cells, gM ctrl=growth medium (DMEM) control; SP=carotenoids contained within strain PD01 spores IV=initial value, i.e. TEER before treatment (0 h).

The results (FIG. 12) showed that the carotenoids from PD01 protect the intestinal barrier against disruption of resistance, while α-tocopherol (a lipophilic plant-derived carotenoid produced from the same precursor) did not induce protection. This surprising effect shows that microbial carotenoids have a modulating effect on the gut barrier function while the plant-derived compound lacks these properties.

Example 6

Figure 13:
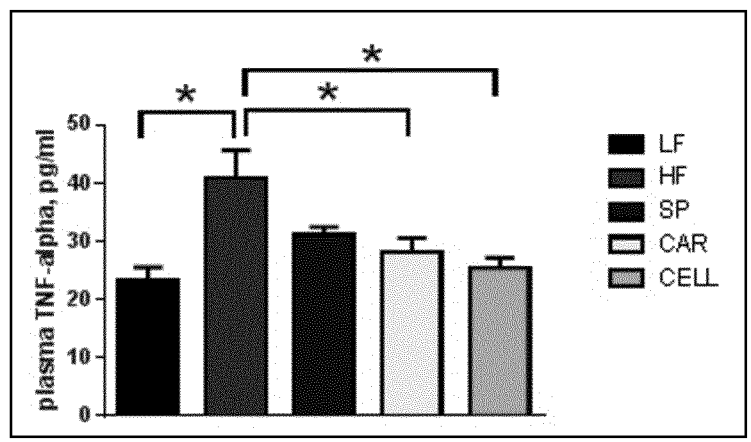
FIG. 13: Plasma TNF-α concentrations (pg/ml) in rats after 8 weeks of treatment with a low-fat diet (LF), a high-fat diet (HF), a high-fat diet and carotenoids contained within PD01 spores (SP), a high-fat diet and carotenoids contained within PD01 vegetative cells (CELL), or a high-fat diet and carotenoids extracted from PD01 (CAR).

Effect of Carotenoids Extracted from Strain PD01 (LMG P-29664) on Inflammatory Status In Vivo The effect of carotenoids from strain PD01 on inflammatory status was evaluated in an in vivo rat experiment with a HF diet condition, as described in Example 4. After 8 weeks of treatment, rats fed with a HF diet exhibited significantly higher plasma TNF-α concentrations than rats fed with the standard LF diet. Surprisingly, co-administration of the HF diet with carotenoids from strain PD01 (either extracted from strain PD01 or contained within strain PD01 vegetative cells or spores) allowed to prevent the development of the pro-inflammatory state, resulting in reduced plasma concentrations of pro-inflammatory cytokine TNF-α as compared to the HF group (FIG. 13). This result shows that the carotenoids from PD01 (irrespective of the specific formulation) can prevent the build-up of inflammation and therefore have immune-protective properties.

Example 7

Effect of Carotenoids Extracted from Strain PD01 (LMG P-29664) on Gastro-Intestinal Symptoms in Humans The effect of carotenoids from strain PD01 on gastro-intestinal symptoms was assessed in a 6-week phase II efficacy study in healthy, but overweight individuals. The study was designed as a randomized, placebo-controlled, double-blind, parallel study. The aim of the study was to investigate the effects of a daily intake of carotenoids from strain PD01 (contained within bacterial spores) with respect to modulation of the gut microbiome. The study population consisted of 60 healthy individuals with BMI 25-35 kg/m$^2$, age 18-70 years. At inclusion, participants were randomized to PD01 or placebo for a period of 6 weeks. Each participant underwent 3 test days at the study site, namely (1) at the start of the study, (2) after 3 weeks of study product supplementation and (3) at the end of the study (after 6 weeks of study product supplementation). The study product was provided on the first test day for the following 6 weeks (until test day 3), at a corresponding daily dose of 5*10$^9$ CFU/day with maltodextrin as carrier material in sachets. The placebo consisted of identical sachets containing only carrier material. Participants were informed regarding the method of administration; one sachet had to be dissolved in 150 mL whole milk and it had to be taken every morning before breakfast at the same time point.

Figure 14:
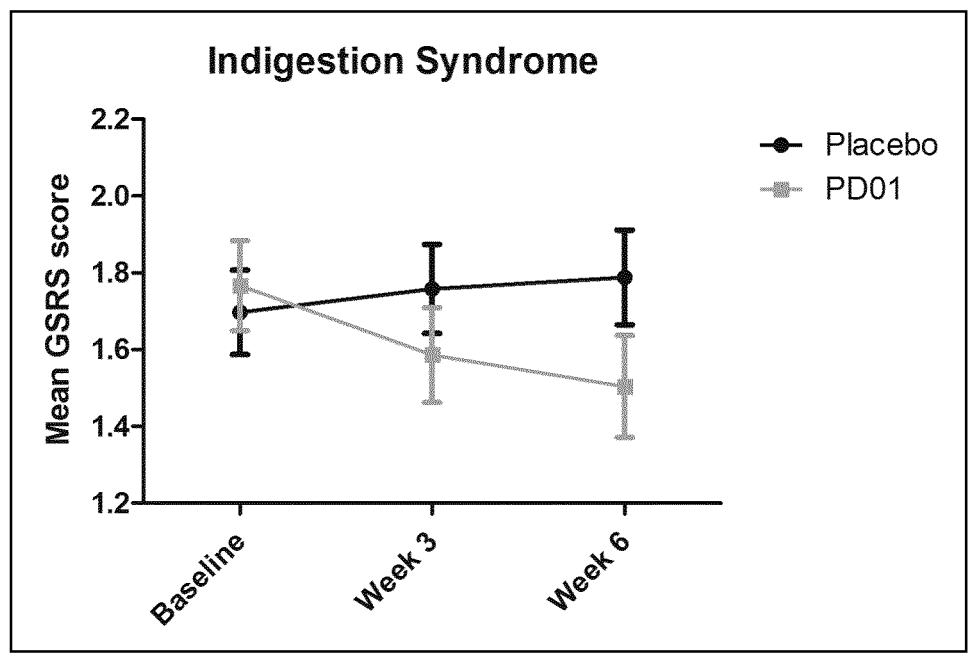
FIG. 14: Change in Gastro-intestinal Symptom Rating Scale (GSRS) score for indigestion syndrome from baseline to end of the study period for PD01-carotenoids-treated and placebo-treated healthy but overweight individuals (n=29 and n=31, respectively). * p<0.1; **p<0.05.

The presence of gastro-intestinal (GI) symptoms was assessed using the validated gastro-intestinal symptom rating scale (GSRS), consisting of 16 items clustered into five major GI syndromes: abdominal pain, reflux, diarrhoea, indigestion and constipation syndrome. Defecation frequency and stool consistency were assessed using the Bristol Stool Form Scale Chart. Subjects were asked to complete these questionnaires at weekly intervals during the study period. Surprisingly, participants receiving daily PD01 scored lower on the GSRS subdimension for indigestion syndrome after 3 weeks of supplementation (p =0.061, FIG. 14), becoming significant at the end of the study period (p=0.045; FIG. 14). This confirms that bacterial carotenoids from strain PD01 can prevent or decrease gastro-intestinal symptoms which are also typically described for IBS.

Example 8

Bioavailability of Carotenoids in Humans

In the phase II study as described in example 7, blood samples were collected for assessment of the concentration of bacterial carotenoids in fasted plasma of the overweight subjects (n=29) before and after 3 and 6 weeks of daily supplementation of carotenoids from strain PD01 (contained within spores, formulated at 5*10$^9$ CFU/day).

Figure 15:
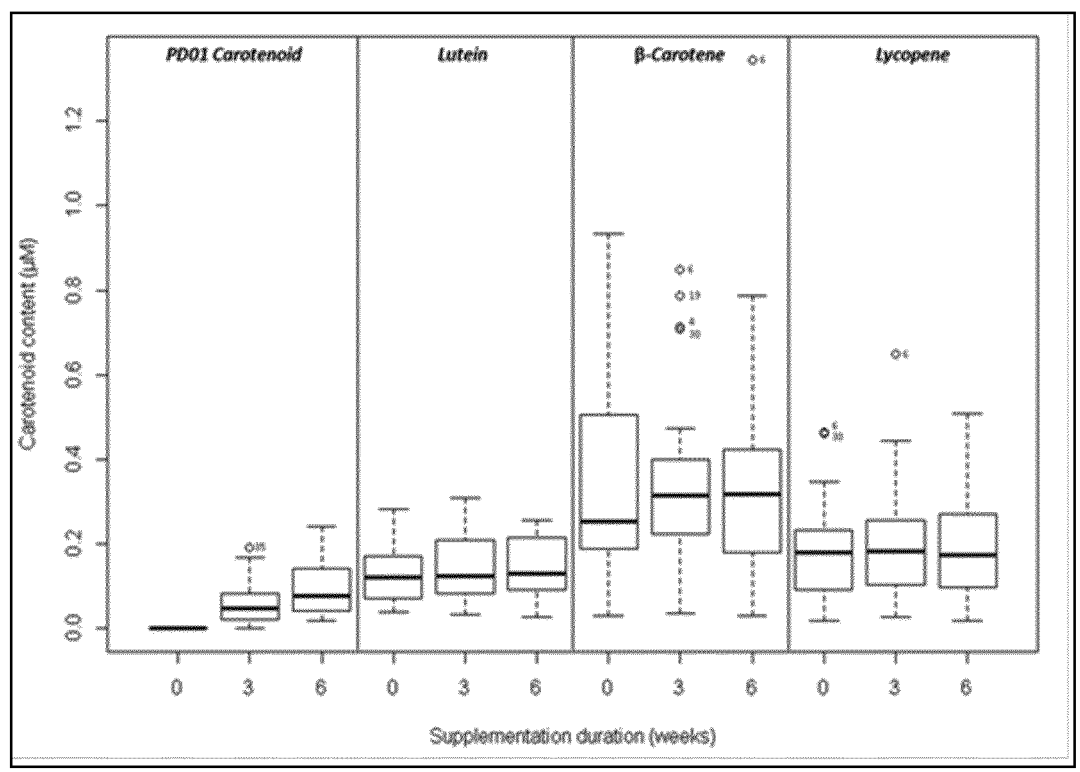
FIG. 15: Carotenoid concentrations in fasted plasma of overweight subjects treated with PD01 (n=29) during the phase II clinical study. Horizontal bars represent medians; boxes represent $25^{th}$-$75^{th}$ percentiles, and whiskers indicate $5^{th}$-$95^{th}$ percentiles. Small circles indicate outliers.

Strain PD01 carotenoids were not detected at baseline, but were present in fasted plasma of all subjects after 3 and 6 weeks of PD01 treatment (FIG. 15). The plasma concentration of PD01 carotenoids significantly increased during the 6 weeks of supplementation (0.044 µM at 3 weeks, 0.076 µM at 6 weeks) (FIG. 15).

This study demonstrated that daily supplementation of carotenoids contained within spores of strain PD01 for a period of 6 weeks led to an accumulation of PD01 carotenoids in plasma. The PD01 carotenoid plasma concentrations were detectable in all subjects, demonstrating that PD01 carotenoids were absorbed. Furthermore, levels of PD01 carotenoids reached a final exposure similar as for lutein. However, while daily intake levels of lutein in Europe are estimated at 1-4 mg/d (healthy, fruit-rich diet), daily intake of PD01 carotenoids was as low as 25 µg/d. This further confirms the surprising superior bioavailability of PD01 carotenoids over plant-derived carotenoids.

Additionally, the carotenoid-producing *Bacillus* strain PD01 was quantified in human feces by plate counts on LB agar plates. Results showed that upon PD01 treatment, the *Bacillus* strain was able to persist in the human colon at concentrations of 3*10$^7$ CFU/g, mostly in the form of vegetative cells (Table 2).

TABLE 2

Enumeration of strain PD01 (CFU/g) in human feces of the PD01 treated subjects from the human intervention trial, prior to the supplementation period (T0), after 3 weeks of daily administration of PD01 (T3) and after 6 weeks of daily administration of strain PD01 (T6). Results are expressed as mean ± SE; n = 29; ND = not detectable.

|  | T0 | T3 | T6 |
|---|---|---|---|
| Total cells (CFU/g) | N.D. | 4.50E+07 ± 1.57E+07 | 2.52E+07 ± 3.88E+06 |
| Spores (CFU/g) | N.D. | 1.36E+07 ± 4.98E+06 | 6.18E+06 ± 1.27E+06 |

Example 9

Effect of Carotenoids Extracted from Strain PD01 (LMG P-29664) on Gut Barrier Function in Humans In the phase II efficacy study as described in example 7, gut barrier function was assessed at baseline and at the end of the study period of 6 weeks by performing a gut permeability test. Participants had to ingest a sugar drink (in 150 mL tap water) containing 1 g sucrose, 1 g lactulose, 0.5 g L-rhamnose, 1 g sucralose and 1 g erythritol after an overnight fast. Before ingestion, a urine sample was collected for baseline sugar analysis. Then, full urine output was collected during 24 hours in three separate fractions, i.e. 0-2, 2-5 and 5-24 hours. Sucrose, lactulose, L-rhamnose, sucralose and erythritol were determined by fluorescent detection high-pressure liquid chromatography as reported in literature.

The study demonstrated that daily supplementation of carotenoids contained within spores of strain PD01 for a period of 6 weeks led to a reduction in sucrose excretion (Table 3), suggesting that PD01 carotenoids improved the permeability of the small intestine. Similar effects were noted for the colon permeability. This result confirms the in vitro observations of the effect of PD01 carotenoids on gut barrier function in humans.

TABLE 3

Sucrose excretion (μmol) and ratios of excreted sugars as measured in urine in the 0-5, 5-24 and 0-24 h fraction from baseline to end of the study period for PD01-carotenoid-treated and placebo-treated individuals (n = 29 and n = 31, respectively). Values between brackets represent 25$^{th}$-75$^{th}$ percentiles. E = erytrhitol; L = lactulose, R = L-rhamnose, S = sucralose

|  | Intervention | Baseline | End |
|---|---|---|---|
| 0-5 h sucrose | Placebo | 5.290 [2.930; 11.625] | 5.030 [3.460; 12.520] |
|  | PD01 | 6.975 [2.140; 19.248] | 4.370 [2.540; 9.575] |
| 0-5 h L/R ratio | Placebo | 0.030 [0.020; 0.040] | 0.030 [0.020; 0.040] |
|  | PD01 | 0.035 [0.020; 0.050] | 0.030 [0.020; 0.040] |
| 5-24 h S/E ratio | Placebo | 0.010 [0.010; 0.020] | 0.010 [0.010; 0.015] |
|  | PD01 | 0.015 [0.010; 0.020] | 0.010 [0.010; 0.020] |
| 0-24 h S/E ratio | Placebo | 0.010 [0.010; 0.020] | 0.010 [0.010; 0.010] |
|  | PD01 | 0.010 [0.010; 0.020] | 0.010 [0.010; 0.020] |

Example 10

Figure 16:
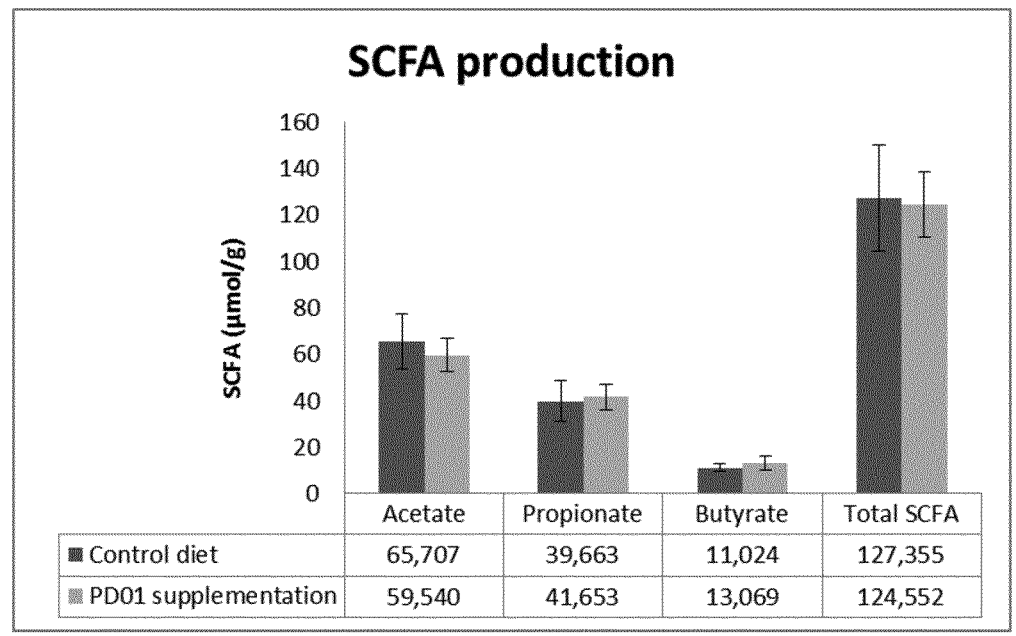
FIG. 16: Total short-chain fatty acid (SCFA) levels (μmol/g) (A) and butyrate over acetate (B/A) ratio (B) in digesta of weaned piglets upon 23-day-supplementation of carotenoids contained within strain PD01 spores as compared to a control diet (n=2×8).
Figure 16:
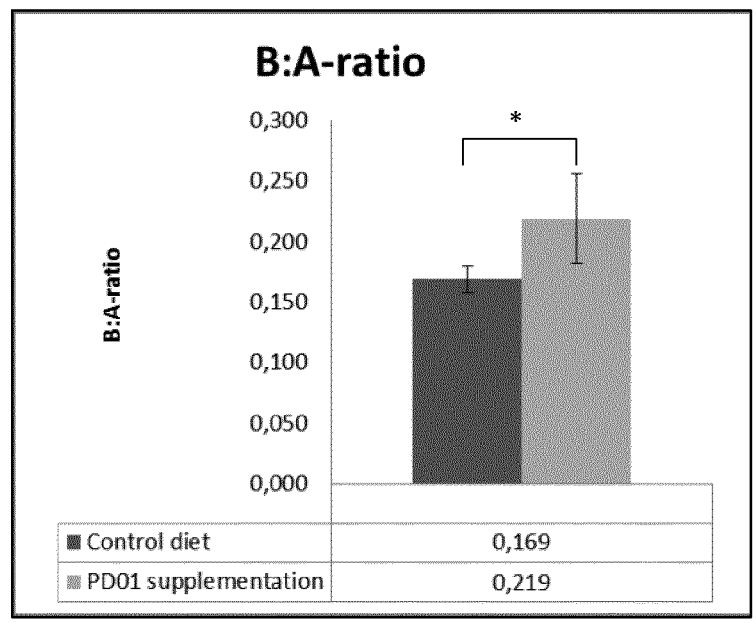

Effect of Carotenoids Extracted from Strain PD01 (LMG P-29664) on Gut Health in Pigs A 3-week study was set up with male and female weaned piglets (weaned at 19 days of age). The study was designed as a randomized, placebo-controlled study with 8 piglets per group. The aim of the study was to investigate the effects of including carotenoids contained within spores of strain PD01 (2*10$^9$ PD01 spores per kg diet) in the diet of weaned piglets, as compared to a control diet, with respect to modulation of the gut microbiome and parameters of gut health. Sixteen weaned piglets were included in the study. At the end of the experiment (23 days), all piglets were sacrificed and digesta from the gastro-intestinal tract and intestinal sections were collected. Digesta of 75-100% of the small intestinal length, cecal digesta, digesta in 20 cm segment preceding the mid-colon and rectum were collected for SCFA analysis. Segments at 50% and 90% of small intestinal length and of the mid-colon were excised and used for Ussing chambers measurements and gene expression analysis to assess the gut barrier integrity. The SCFA results showed that while no or minor changes in the total SCFA production were reported (FIG. 16A), administration of carotenoids from PD01 altered the SCFA profiles by inducing a shift from acetate to the health-promoting SCFA butyrate (FIG. 16B). This result confirms the in vitro observations of the effect of PD01 carotenoids.

Measurements in Ussing chambers showed significant effects and tendencies on gut barrier integrity parameters after the administration of carotenoids contained within spores of strain PD01 (Table 4). Both in the distal small intestine and mid-colon the integrity of the tissue, as assessed by TEER, was higher after administration of PD01 carotenoids as compared to the control diet. Corroborating with that, numerical decreases of paracellular permeability ($P_{app}$ FD-4) were found after administration of PD01 carotenoids at both sites of the GIT.

Figure 17:
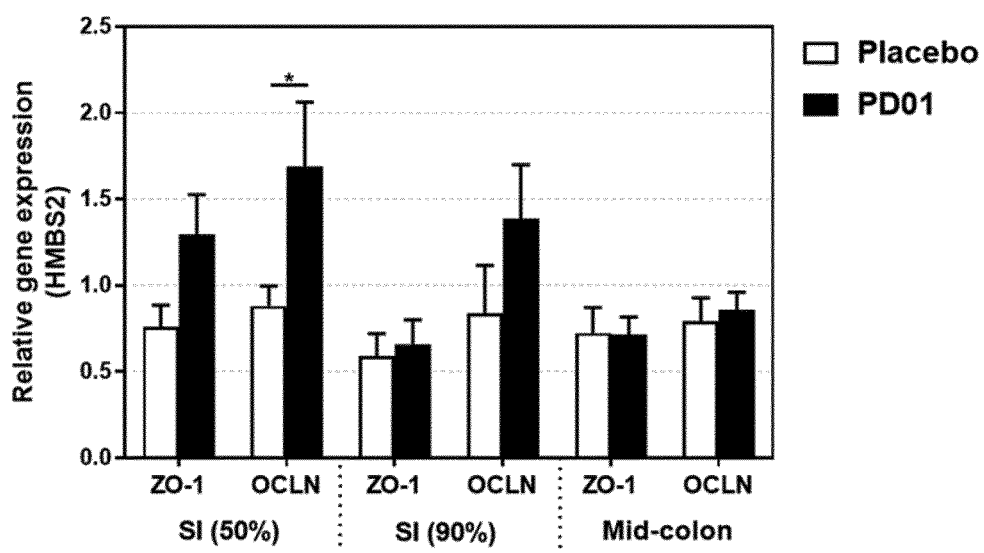
FIG. 17: Relative gene expression of tight-junction TJP1 and OCLN (normalized on the expression of HBMS2) in intestinal tissue of weaned piglets upon 23-day-supplementation of carotenoids contained within strain PD01 spores as compared to a control diet (n=2×8). *p<0,1; SI (50%), SI (90%): 50%, 90% of small intestinal length.

In addition, a higher expression of ZO-1 (zonula occludens 1 or Tight junction protein 1 (TJP1)) and OCLN (Occludin) was observed in the small intestine of piglets within the PD01 group when compared to placebo, particularly in the segments at 50% of intestinal length and for Occludin (FIG. 17). Thus, PD01 carotenoids exert a protective effect on intestinal barrier function by increasing the expression of tight junction proteins. This is in line with the results obtained with the Ussing chambers and the gut permeability test described in Example 9.

TABLE 4

Effect of experimental diets fed to weaners on characteristics of small intestinal mucosa and mid-colon determined in Ussing chambers (n = 2 × 8). PappFD-4 = apparent permeability for FITC-4 kDa; SEM = standard error of the mean; TEER = transepithelial electrical resistance of tissue

| Tissue | Parameter | Control diet | Diet supplemented with PD01 carotenoids | SEM | p-value |
|---|---|---|---|---|---|
| Distal small intestine | TEER (Ω cm$^2$) | 36.6 | 45.0 | 2.9 | 0.073 |
|  | $P_{app}$ FD-4 (10$^{-7}$ cm/s) | 13.4 | 9.9 | 2.4 | 0.336 |
| Mid-colon | TEER (Ω cm$^2$) | 22.0 | 34.1 | 2.4 | 0.013 |
|  | $P_{app}$ FD-4 (10$^{-7}$ cm/s) | 23.6 | 16.9 | 3.8 | 0.238 |

Example 11

Superior Effect of Carotenoids Extracted from Strain PD01 (LMG P-29664) Over Plant-Derived Carotenoids on Gut Microbiome Composition and Intestinal Barrier Integrity In order to assess the difference in bioactivity profile between carotenoids from strain PD01 and plant-derived carotenoids, experiments were set up as described in examples 2, 3, 5 and 10.

The effect of carotenoids from PD01, lutein, β-carotene and lycopene on butyrate production in the intestine was assessed in a SHIME experiment as described in example 2. In practice, the different carotenoids were administered daily at the same dosage level to parallel SHIME units for a period of 2 weeks and SCFA levels were monitored.

The effect of carotenoids from strain PD01, lutein, β-carotene and lycopene on gut microbiome composition was assessed in a SHIME experiment as described in example 3. In practice, the different carotenoids were administered daily at the same dosage level to parallel SHIME units for a period of 2 weeks and levels of butyrate-producing bacterial groups were monitored using QPCR as well as bacterial DGGE fingerprints.

The effect of carotenoids from strain PD01, lutein, β-carotene and lycopene on in vitro gut barrier function was assessed using Caco-2/THP1X6 co-cultures, as described in example 5. Endpoint of the measurement was a change from control in the transepithelial electrical resistance (TEER) in a transwell setup upon administration of the different carotenoids at the same dosage level to parallel experiments.

The effect of carotenoids from PD01 or lutein on parameters associated with gut microbiome composition and gut health were described in a piglet study as described in example 10.

Example 12

Effect of Carotenoids Extracted from Strain PD01 (LMG P-29664) on Gut Inflammation in Pigs A 3-week study was set up with male and female weaned piglets (weaned at 19 days of age) as described in Example 10. The study was designed as a randomized, placebo-controlled study with 8 piglets per group. The aim of the study was to investigate the effects of including carotenoids contained within spores of strain PD01 ($2*10^9$ PD01 spores per kg diet) in the diet of weaned piglets, as compared to a control diet, with respect to modulation of the inflammatory tone. Sixteen weaned piglets were included in the study. At the end of the experiment (23 days), all piglets were sacrificed and intestinal sections were collected. Segments at 90% of small intestinal length and of the mid-colon were excised and prepared for gene expression analysis of the pro-inflammatory cytokine IL-1a (Interleukin 1 alfa).

Figure 18:
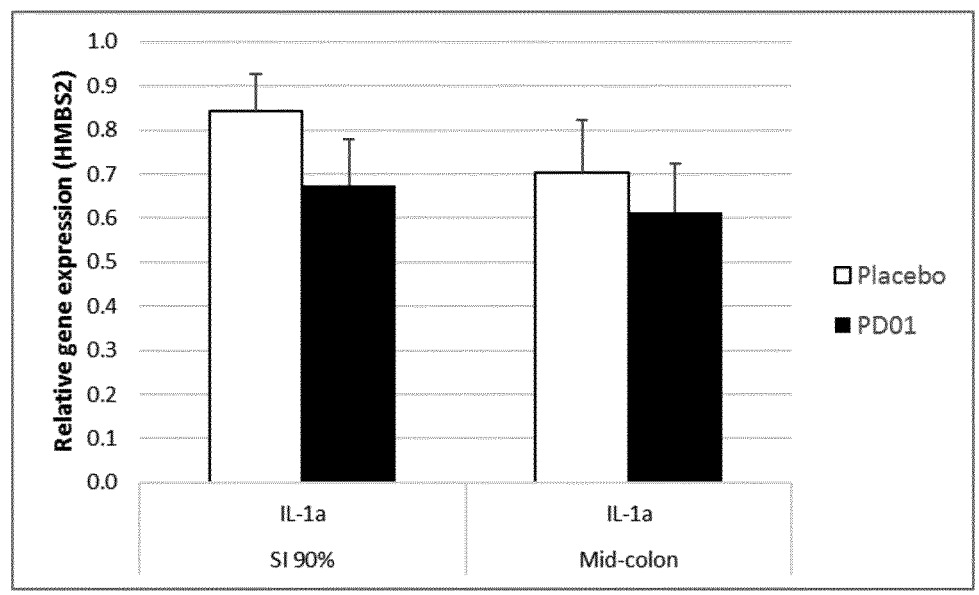
FIG. 18: Relative gene expression of IL-1a in intestinal tissue of weaned piglets upon 23-day-supplementation of carotenoids contained within strain PD01 spores as compared to a control diet (n=2×8). SI (90%): 90% of small intestine length.

As shown in FIG. 18, the expression of IL-1a was lowered in the distal small intestine and mid-colon of piglets within the PD01 group when compared to placebo. Administration of PD01 carotenoids dampens gut inflammation in weaned piglets as also seen in rats fed a HF diet (Example 6).

Example 13

Effect of Carotenoids Extracted from Strain PD01 (LMG P-29664) on the Inflammatory Tone in Peripheral Blood Mononuclear Cells (PBMCs) In Vitro To better understand the immunomodulatory properties of PD01 carotenoids, these were dosed in vitro to peripheral blood mononuclear cells (PBMCs) isolated from 2 healthy donors. The cytokine release by PBMCs was measured upon activation with LPS (500 ng/mL) and compared amongst treatments. The latter entailed exposure to PD01 carotenoids contained within either frozen vegetative cells ($10^7$ cfu/mL) or spores freeze-dried on maltodextrin ($10^7$ cfu/mL), or purified carotenoids extracted from strain PD01 (6.25 µg). In addition, vegetative cells from *Bacillus clausii* (no carotenoids, $10^7$ cfu/mL), a well-know sporulating probiotic strain, β-carotene at 2 strengths (26.75 µg and 66.88 µg), the vehicle used to dissolve the purified PD01 carotenoids and β-carotene (tetrahydrofuran/0.025% butylated hydroxytoluene as reported by Palozza, P. et al., Free Radical Biology & Medicine, vol 30, pp 1000-1007 (2001)), and complete medium (no carotenoids) were included as controls. The LDH assay did not reveal cytotoxicity upon treatment.

Figure 19:
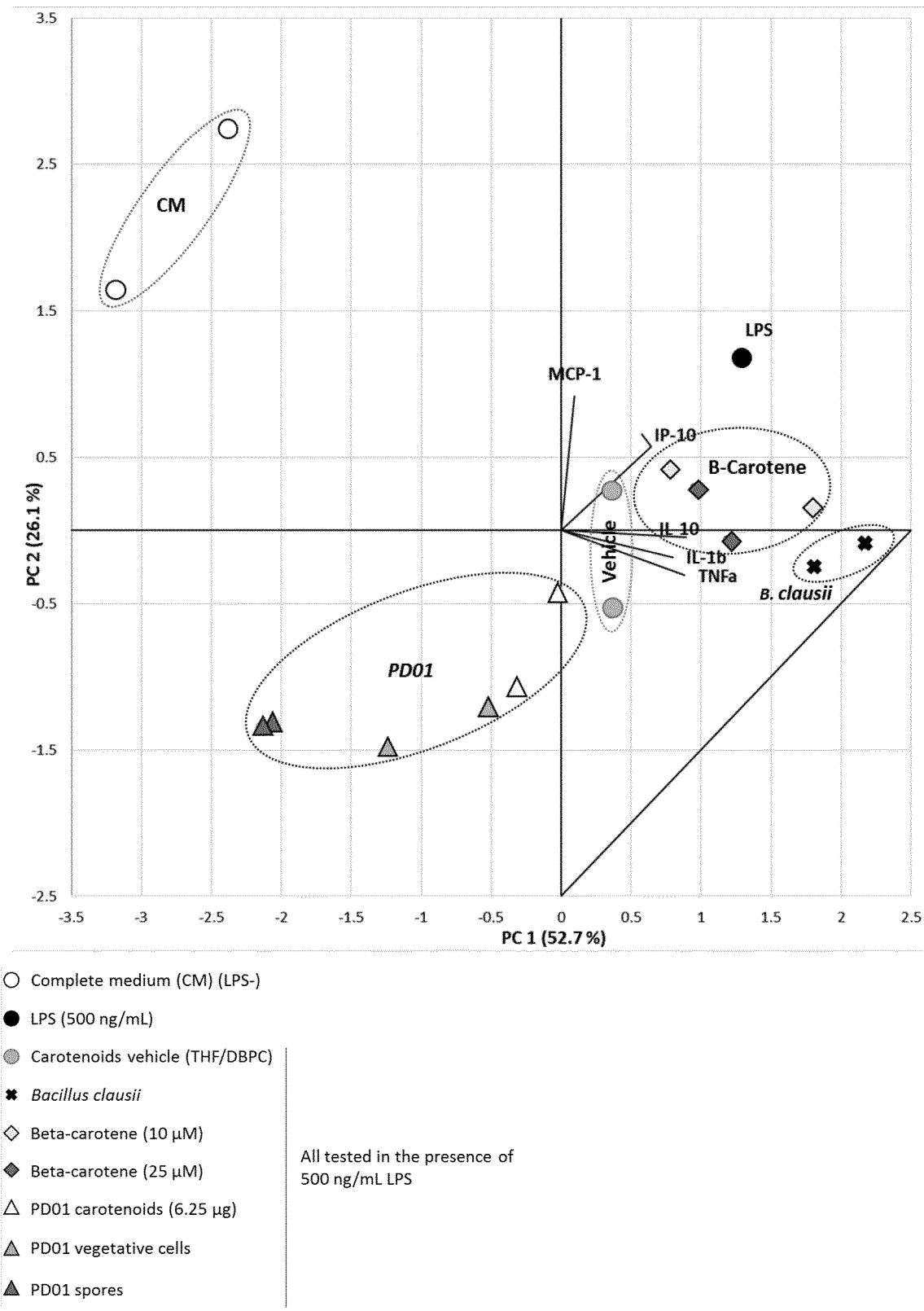
FIG. 19: Principle Component Analysis (PCA) of the immunomodulatory response of PBMCs upon exposure to LPS alone or LPS and PD01 carotenoids either extracted from or contained within strain PD01 vegetative cells or spores; LPS and beta-carotene at 10 μM or 25 μM; LPS and Bacillus clausii vegetative cells; LPS and vehicle; as compared to untreated cells in complete medium (CM) (n=2 donors, 3 wells/treatment).

The readouts of these incubations (IL-1β; TNFα, IL-10, IP-10 (or CXCL-10), and MCP-1 levels), normalized to those of untreated LPS-induced PBMCs, were summarized in a PCA plot (FIG. 19; PC1 52.7% and PC2 26.1%). All 3 treatments involving PD01 carotenoids clustered together and triggered a surprisingly pronounced anti-inflammatory response as compared to β-carotene, the vehicle, *Bacillus clausii* vegetative cells, and LPS itself. Again, these results confirm the superior bioactivity of the microbial PD01 carotenoids as compared to plant-derived β-carotene as a stronger anti-inflammatory response was induced with lower exposure levels. Furthermore, without carotenoids, *Bacillus clausii* cells were not able to elicit a similar response while purified PD01 carotenoids did.

The invention claimed is:

1. A method for treating a disorder associated with disturbed intestinal barrier integrity in a subject in need thereof, the method comprising administering to the subject a composition comprising microbial carotenoid compounds derived from a bacterial species selected from the group consisting of *Bacillus, Staphylococcus, Streptococcus, Methylobacterium, Rubritalea*, and *Sporosarcina*, the microbial carotenoid compounds having formula (I)

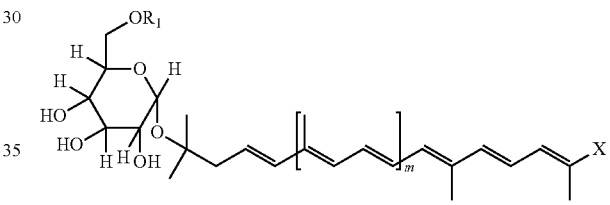

wherein X is $CH_3$ or $COOR_2$ wherein $R_2$ is independently selected from methyl, ethyl, methylethyl, propyl, isopropyl, butyl, isobutyl, sec-butyl and tert-butyl, and wherein m is selected from 0, 1, 2 or 3, and wherein $R_1$ is $COC_nH_{2n+1}$ with n selected from 5, 6, 7, or 8; and wherein the disorder associated with disturbed intestinal barrier integrity is selected from the group consisting of: irritable bowel syndrome, colitis, inflammatory bowel disease, coeliac disease, and any combination thereof.

2. The method of claim 1, wherein X is $CH_3$ or $COOCH_3$, and wherein m is 3, and wherein $R_1$ is $COC_nH_{2n+1}$ with n selected from 5, 6, 7, or 8.

3. The method of claim 2, wherein X is $CH_3$ and $R_1$ is $COC_nH_{2n+1}$ with n=7.

4. The method of claim 2, wherein X is $COOCH_3$ and $R_1$ is $COC_nH_{2n+1}$ with n=5, 6, 7, or 8.

5. The method of claim 1, wherein the microbial carotenoid compound is derived from a *Bacillus indicus* species.

6. The method of claim 1, wherein the subject is a mammal, a fish or a bird.

7. The method of claim 1, wherein the subject is a human.

8. The method of claim 1, wherein the subject is a pet or a farm animal selected from the group consisting of a pig, a sheep, a goat, a cow, a horse, a chicken, a duck, a goose, a turkey, and a rabbit.

9. The method of claim 1, wherein treating the disorder associated with disturbed intestinal barrier integrity in the subject comprises:

stimulating the growth and/or activity of one or a limited number of beneficial bacteria in the intestinal tract;

inhibiting the growth and/or activity of one or a limited number of pathogenic bacteria in the intestinal tract;

increasing the attachment of non-pathogenic bacteria to the mucosa of the gastro-intestinal surface;

reducing uncontrolled uptake of antigens, pro-inflammatory bacteria or bacterial products by the gut;

providing anti-inflammatory activity at the intestinal surface;

increasing gut barrier functions; and/or producing health-beneficial microbial metabolites.

* * * * *